United States Patent [19]

Martel et al.

[11] Patent Number: 4,772,683
[45] Date of Patent: Sep. 20, 1988

[54] HIGH PERCENTAGE BETA-YIELD SYNTHESIS OF CARBAPENEM INTERMEDIATES

[75] Inventors: Alain Martel, Delson; Jean-Paul Daris, St-Hubert; Jacques Corbeil, Montreal, all of Canada

[73] Assignee: Bristol-Myers Company, New York, N.Y.

[21] Appl. No.: 832,191

[22] Filed: Feb. 24, 1986

[51] Int. Cl.$^4$ .................. C07D 205/08; C07D 401/12; C07D 403/12; C07F 7/18
[52] U.S. Cl. ...................................... 540/200; 546/14; 546/341; 548/110; 548/214; 548/342; 549/4; 549/79; 549/214; 549/499; 556/423
[58] Field of Search ......................................... 540/200

[56] References Cited

U.S. PATENT DOCUMENTS 4,683,296  7/1987  Ueda et al. .......................... 540/350

OTHER PUBLICATIONS

Shih, David H., et al., *Heterocycles*, (vol. 21, No. 1, 1984), pp. 29-40.
Merck, *Drugs of the Future*, (Vol. 9, No. 5, 1984) pp. 3360338 at 337.
Kim, *Tet. Letters*, 28, 507-510, (1987).
Tajima, *Tet. Letters*, 26(5), 673-676, (1985).
Gennari et al., *Tet. Letters*, 26 (6), 797-800, (1985).

Primary Examiner—Mark L. Berch
Attorney, Agent, or Firm—R. E. Carnahan

[57] ABSTRACT

Disclosed herein is a novel process using novel silyl enol ether intermediates of the formula

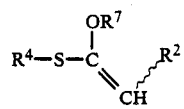

to generate novel azetidione thiolester intermediates of the formula

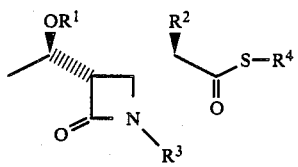

which can be used to form 1-$\beta$-alkyl carbapenem antibiotics. It has now been discovered that if the R$^4$ group is selected from a small group of moieties having the formula:

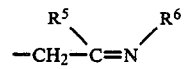

an increased $\beta$-yield of up to approximately 100% can be obtained.

13 Claims, No Drawings

HIGH PERCENTAGE BETA-YIELD SYNTHESIS OF CARBAPENEM INTERMEDIATES

BACKGROUND OF THE INVENTION

1. Field of the Invention

The present invention is directed to a novel process for producing novel intermediates useful in the synthesis of 1-β-alkyl carbapenems.

2. Description of the Prior Art

A wide variety of carbapenems, such as the natural fermentation product thienamycin (Formula I), have been reported in the patent and scientific literature as having exceptional antibacterial activity.

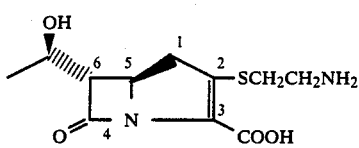

However, researchers attempting to develop thienamycin have encountered two problems, namely: (1) the compound is very difficult to ferment and isolate, and (2) the product is very unstable, such that it reacts with itself and decomposes. To circumvent these problems, carbapenem derivatives have been prepared which possess excellent stability and antibacterial spectra.

One such group of derivatives currently being investigated is the 1-β-methyl carbapenems of the formula:

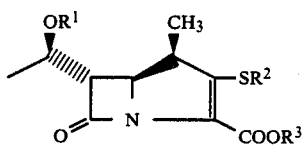

wherein $R^1$ is hydrogen or a conventional hydroxy-protecting group; and $R^2$ and $R^3$ are independently selected from the group consisting of substituted and unsubstituted: alkyl, alkenyl and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; spirocycloalkyl having 3–6 carbon atoms; phenyl; aralkyl, aralkenyl and aralkynyl wherein the aryl moiety is phenyl and the aliphatic portion has 1–6 carbon atoms; heteroaryl, heteroaralkyl, heterocyclyl and heterocyclylalkyl wherein the hetero atom or atoms in the above-named heterocyclic moieties are selected from the group consisting of 1–4 oxygen, nitrogen and sulfur atoms and the alkyl moieties associated with said heterocyclic moieties have 1–6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1–6 carbon atoms.

Recently reported synthetic schemes for producing 1-β-methyl carbapenems of Formula II, such as those of Shih et al., *Heterocycles*, volume 21, no. 1, pages 29–40 (1984), proceed through intermediates of the formula

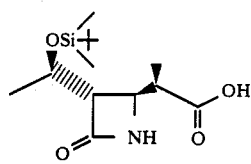

from which the 1-β-methyl carbapenems can be formed easily and in high yield. Unfortunately, however, these schemes require numerous other intermediates and time consuming steps to produce the above intermediate, each of which increases the process time and decreases the overall yield. Furthermore, the steps required to produce β-methyl intermediate III also produce a large amount of the corresponding α-methyl product. Accordingly, there is a need for a stereoselective process which provides a high percentage β-yield (the yield of β-product/the total yield of product) of intermediates which can easily be converted to 1-β-alkyl carbapenems.

One recent process of interest described by Tajima et al, in *Tetrahedron Letters*, volume 26, no. 5, pp. 673–676 (1985), discloses the reaction of silyl enol ether intermediates with 4-acetoxyazetidinone to produce compounds of the formula

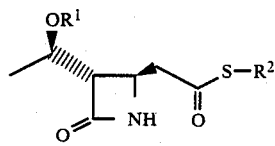

wherein $R^1$ is a hydroxy-protecting group, and $R^2$ is selected from the group consisting of

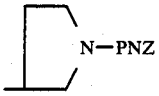 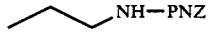

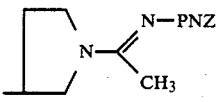

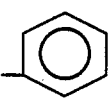 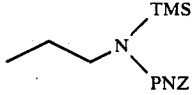

wherein PNZ is p-nitrobenzyloxycarbonyl, and TMS is trimethylsilyl.

This procedure has been viewed with interest because it bypasses several steps of conventional carbapenem syntheses. However the interest has been limited because practioners now wish to produce 1-β-alkyl carbapenem intermediates, and Tajima et al provides no guidance for a stereoselective process which provides a high percentage β-yield of such intermediates.

Other procedures, such as those disclosed in U.S. patent application Ser. No. 725,594 filed Apr. 22, 1985, and now U.S. Pat. No. 4,683,296 patented July 28, 1987, which is a continuation-in-part of U.S. patent application Ser. No. 472,443 filed Mar. 7, 1983, use silyl enol ether precursors for preparing 1-β-alkyl carbapenem intermediates. These processes, however, do not use azetidinone thiolesters and thus provide no guidance for processes which do.

Accordingly, it would be desireable to produce azetidinone thiolester intermediates by a silyl enol ether process, which intermediates can be used to produce 1-β-alkyl carbapenems. Furthermore, it would be desireable that such process be stereoselective and provide a high percentage β-yield.

SUMMARY OF THE INVENTION

This invention is directed to novel intermediates and a novel high β-yield process for preparing intermediates useful in the synthesis of 1-β-alkyl carbapenems, which novel intermediates have the formula

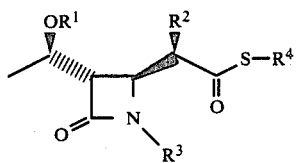

wherein
$R^1$ is hydrogen or a conventional hydroxy-protecting group,
$R^2$ is a lower alkyl having from 1-6 carbon atoms,
$R^3$ is hydrogen or a triorganosilyl group, and
$R^4$ represents a group of the formula

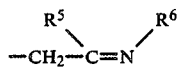

wherein $R^5$ and $R^6$ independently, or taken together, are selected from the group consisting of hydrogen, substituted and unsubstituted: alkyl, alkenyl and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms, providing that when $R^5$ and $R^6$ are taken together to form said heterocycylic moiety, said moiety contains at least one hetero nitrogen atom, and the alkyl moieties associated with said heterocyclic moieties have 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms, and
which process comprises the steps of:
(A) reacting a compound of the formula

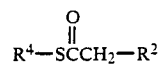

wherein $R^2$ and $R^4$ are as defined above,
with a triorganosilyl triflate silylating agent to yield a silyl enol ether intermediate of the formula

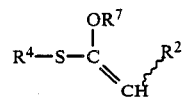

wherein $R^2$ and $R^4$ are as defined above, $R^7$ is a triorganosilyl group, and
(B) reacting Compound 8 with a compound of the formula

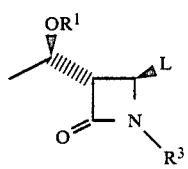

wherein
$R^1$ and $R^3$ are as defined above, and
L is a leaving group capable of being displaced by nucleophilic substitution of Compound 8.

Saponification of Compound 12 yields the corresponding carboxylic acid, from which 1-β-alkyl carbapenems can be synthesized using well-known methods.

Normally, processes similar to the above process can be expected to yield a racemic mixture of intermediate 12, i.e., a mixture of geometric isomers wherein $R^2$ is in either the α- or β-configuration. Since the desired final product, i.e., the carbapenem, is of the β-configuration, a high β-yield of intermediate 12 is desireable. Unfortunately, however, previous attempts to obtain high β-yields have failed since most $R^4$ groups provide the α-isomer as the predominant product.

Surprisingly, it has been discovered that if $R^4$ is selected from a small group of moieties having the formula:

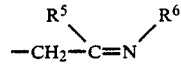

wherein $R^5$ and $R^6$ are as defined above, an increased β-yield of up to approximately 100% can be obtained.

DETAILED DESCRIPTION OF THE INVENTION

The process for preparing the intermediates of this invention may conveniently be summarized by the following reaction sequence of Diagram 1. In this reaction, the silyl enol ether 8 of thioester 6 is generated in Step (A), and without separation is coupled, in Step (B), to azetidinone 10 by nucleophilic displacement of the 4-position leaving group "L". The resulting intermediate 12 (illustrated in the β-isomer form) can then be saponified in Step (C) to yield the corresponding carboxylic acid 14, which can be converted to a 1-β-alkyl carbapenem by reported procedures. Diagram 1 is as follows:

DIAGRAM 1

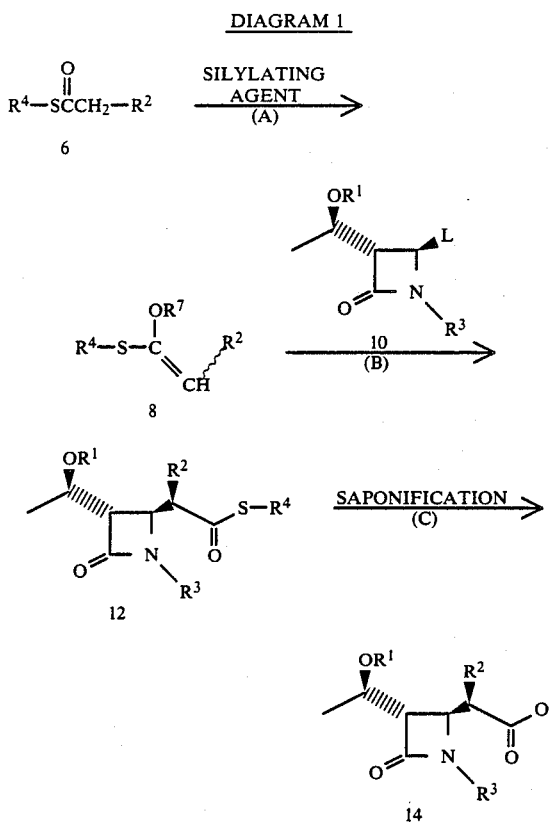

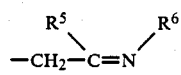

Referring now to Diagram 1, Step (A) illustrates the reaction between thioester 6 and a triorganosilyl triflate silylating agent to form the silyl enol ether 8. The reaction of Step (A) is carried out in an inert organic solvent and in the presence of an organic base. Suitable inert organic solvents which can be used include methylene chloride, tetrahydrofuran, carbon tetrachloride, cyclohexane, dioxane, dimethoxyethane, diethyl ether and chloroform. Reaction temperatures can be the range of from about −40° C. to +30° C. Most conveniently the reaction is carried out by mixing the reactants under cooling, advantageously between about −15° C. and 0° C., and then allowing them to gradually warm to room temperature.

Triorganosilyl triflate silylating agents are well known, and include trimethylsilyl trifluoromethanesulfonate, triisopropylsilyl trifluoromethanesulfonate, triethylsilyl trifluoromethanesulfonate, t-butyldimethylsilyl trifluoromethanesulfonate, t-butyldiphenylsilyl trifluoromethanesulfonate, or 2,4,6,-tri(t-butylphenoxy)dimethylsilyl trifluoromethanesulfonate. Advantageous results have been obtained using t-butyldimethylsilyl trifluoromethanesulfonate. Thus, $R^7$ will be the triorganosilyl residue of the particular triorganosilyl triflate silylating agent used.

Suitable organic amine bases include diisopropylethylamine, DBU (1,8-diazabicyclo[5.4.0]undec-7-ene), DBN (1,5-diazabicyclo[4.3.0]non-5-ene), but especially preferred are the tri($C_1$-$C_4$)alkylamines such as trimethylamine, triethylamine, tributylamine and tripropylamine. It has been found, however, that in at least one instance a stronger base should be used to carry out the reaction of Step (A). When 3-methyl-2-(propionylthiomethyl)-pyridine is the thioester used, a stronger base such as lithium hexamethyl disilazane or lithium diisopropyl amide is advantageously used. (See Example 4).

Generally, the organic base and triorganosilyl triflate silylating agent are present in an approximately twofold molar excess when compared to the thioester 6, with the base being slightly in excess of the triorganosilyl triflate silyating agent. Reaction times usually vary from about one hour to about five hours, but generally a maximum yield will be obtained in about three hours. In one instance, however, a 70 hour reaction time was used to obtain maximum yield (Example 2). Advantageously, the reaction is carried out under an inert atmosphere.

As stated above, $R^2$ is lower alkyl having from 1-6 carbon atoms, but advantageously is methyl since 1-β-methyl carbapenems have been found to posess excellent antibiotic properties. $R^3$ is hydrogen or a triorganosilyl group, and $R^4$ is a group of the formula $$-CH_2-C\overset{R^5}{\underset{}{=}}N\overset{R^6}{\underset{}{}}$$

wherein $R^5$ and $R^6$ independently, or taken together, are selected from the group consisting of hydrogen, substituted and unsubstituted: alkyl, alkenyl and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms, providing that when $R^5$ and $R^6$ are taken together to form said heterocyclic moiety, said moiety contains at least one hetero nitrogen atom, and the alkyl moieties associated with said heterocyclic moieties have 1-6 carbon atoms; wherein the substituent or substituents relative to the above-named radicals are selected from the group consisting of: amino-, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms.

Advantageously, however, $R^5$ and $R^6$ are taken together and $R^4$ represents a group selected from the group consisting of substituted and unsubstituted: heteroaryl, heteroaralkyl, heterocyclyl and heterocyclylalkyl wherein the hetero atom or atoms in the above-named heterocyclic moieties includes at least one nitrogen and the remaining hetero atoms, if any, are selected from the group consisting of 1-4 oxygen, nitrogen and sulfur atoms and the alkyl moieties associated with said heterocyclic moieties have 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms.

More advantageously, $R^4$ is selected from the group consisting of 5 or 6 membered heterocyclic rings such as 2-picolyl (Example 1); 2-methylene-3-methylpyridine (Example 4); 3-methyleneisothiazole (Example 9); and 1-methyl-2-methyleneimidazole (Example 11). These groups have proven to be stable and to provide excellent β-yields. The most advantageous $R^4$ is 2-methylene-3-methylpyridine (Example 4), which yields approximately 100% of the β-isomer of intermediate 12.

In Step (B), the silyl enol ether 8 is reacted with a 4-position substituted azetidinone 10 to yield intermediate 12. The reaction is carried out in the presence of a Lewis acid catalyst and a solvent which is inert in the presence of the Lewis acid catalyst.

Suitable inert solvents, which are discussed above, are advantageously dry, and will generally comprise about 10% of the total reaction mixture volume. Dichloromethane has been found to provide satisfactory results.

Suitable Lewis acid catalysts include zinc halides, zirconium halides and boron trifluoride. Zinc chloride has been found to provide satisfactory results.

Azetidinone 10 is substituted by a leaving group "L" in the 4-position, a hydrogen or conventional hydroxy-protecting group in the 3-position, and a hydrogen or triorganosilyl group on the 1-position nitrogen.

Hydroxy-protecting groups, which are known to those skilled in the art, are desirable because they prevent side reactions and provide increased yields in later steps of the reaction sequence. Suitable hydroxy-protecting groups may be, for example, acyl groups such as benzyloxy-carbonyl, benzhydryloxycarbonyl, trityloxycarbonyl, p-nitro-benzyloxycarbonyl and 2,2,2-trichloroethoxycarbonyl, aralkyl groups such as benzyl, benzhydryl, trityl or p-nitrobenzyl or triorganosilyl groups such as tri($C_1$-$C_6$)alkylsilyl (e.g. trimethylsilyl, triethylsilyl, triisopropylsilyl, isopropyldimethylsilyl, t-butyldimethylsilyl, methyldiisopropylsilyl or methyldi-t-butylsilyl), triarylsilyl (e.g. triphenylsilyl, tri-p-xylylsilyl) or triaralkylsilyl (e.g. tribenzylsilyl). Examples of these and other suitable hydroxy-protecting groups and methods for their formation and removal are known in the art, e.g. see *Protective Groups in Organic Synthesis*, T. W. Greene, John Wiley & Sons, New York, 1981, Chapter 2.

The hydroxy-protecting group selected is preferably one that is removable at a later stage of the reaction process. Bulky triorganosilyl groups such as triisopropylsilyl, t-butyldiphenylsilyl or t-butyldimethylsilyl are advantageously employed because they provide for an essentially stereo-controlled reduction step. Such groups can be readily removed under mild conditions, e.g. by treatment with methanolic HCl or with fluoride ion (e.g. tetra-n-butyl ammonium fluoride/tetrahydrofuran), which preserves the sensitive β-lactam nucleus.

The 4-position substituent of Compound 10 is designated by "L", which represents a leaving group capable of being displaced by nucleophilic substitution of the silyl enol ether 8. Such leaving groups include acyloxy (e.g., acetoxy, propionyloxy or t-butyryloxy), halogen (e.g., chloro), arylsulfonyl (e.g., phenylsulfonyl), mesyl, tosyl, etc. Advantageously, "L" is acetoxy because 4-acetoxyazetidinone is a readily available starting material.

The 1-position nitrogen substituent $R^3$ is normally a hydrogen, but can alternatively be a triorganosilyl group (e.g., trimethylsilyl), which is described above.

Carbapenem syntheses using triorganosilyl groups on the 1-position nitrogen are well known (e.g., Merck, *Drugs of the Future*, volume 9, no. 5, pp 336–338, at 337, 1984).

The reaction of Step (B) is advantageously carried out under an inert atmosphere, and at a temperature of from about −30° C. to about room temperature. Advantageously, the reactants are added under cooling, about −15° C. to about +5° C. and allowed to gradually warm to room temperature. After warming, the reaction can be stirred for up to 30 hours to achieve maximum yield.

Generally, the zinc chloride and the 4-substituted azetidinone 10 are reacted in approximately equimolar amounts. The silyl enolate 8 is advantageously present in an excess of at least about 1.5 to about 3 mole equivalents per equivalent of azetidinone 10.

The α- and β-isomers of the resulting intermediate 12 can be separated by HPLC. Alternatively, the β-isomer can be separated from the α-isomer upon saponification of intermediate 12, which yields the corresponding carboxylic acid 14 because the β-isomer preferentially crystallizes when the β/α yield is about 2/1 or greater.

In Step (C), Compound 12 is saponified to yield the corresponding carboxylic acid 14. Saponification is a well known procedure of organic chemistry and can be carried out as follows. Compound 12 can first be dissolved in a solvent such a 2:1 mixture of THF/water. Then, under cooling, an excess of inorganic base, such as sodium hydroxide, is added. Hydrogen peroxide may also be added. The reaction is usually complete within about 30 minutes. The carboxylic acid 14 is yielded upon subsequent acidification with an inorganic acid such as hydrochloric acid. A similar saponification is described by Shih et al, *Heterocycles*, volume 21, no. 1, pp 29–40, at 31 (1984).

Tables 1 and 2, and the 17 Examples which follow, illustrate the results of numerous experimental reactions carried out in accordance with the process of this invention. The results of these reactions illustrate the dramatic effect of the $R^4$ substituent on the β-yield of intermediate 12. In these reactions, $R^1$ is t-butyldimethylsilyl, $R^3$ is hydrogen, and t-butyldimethylsilyl trifluoromethanesulfonate is the silylating agent used.

Table 1 is a compilation of the β/α yield, and the overall yield (in percent by weight) obtained in Examples 1–15, wherein $R^2$ is methyl. This table facilitates comparison of the effect of various $R^4$ groups on the β-yield of intermediate 12. Most noticeable are Examples 4 and 5 wherein a 100% yield of the β-methyl isomer is obtained using a 2-methylene-3-methylpyridine group as $R^4$. Table 1 is as follows:

TABLE 1

FORMATION OF COMPOUND 12 WITH

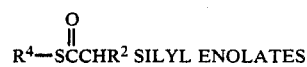
SILYL ENOLATES

| EXAMPLE | $R^4$ | B/A RATIO | YIELD(PBW) |
|---|---|---|---|
| 1 | 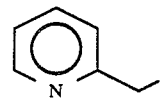 | 87/13 | 88.6(oil) 80.0(crystal) |

TABLE 1-continued

FORMATION OF COMPOUND 12 WITH

R⁴—S(C=O)CHR² SILYL ENOLATES

| EXAMPLE | R⁴ | B/A RATIO | YIELD(PBW) |
|---|---|---|---|
| 2 | furan-CH₂- | 15/85 | 100 |
| 3 | (CH₃)₂N-CH₂- | 1/1 | 49 |
| 4 | 3-methyl-2-pyridyl-CH₂- | 100/0 | 97 |
| 5A | ISOMER A | 9/1 | 33 |
| 5B | ISOMER B | 100/0 | 55 |
| 6 | thiophene-CH₂- | 19/81 | 84 |
| 7 | phenyl-CH₂- | 1/9 | 91 |
| 8 | t-BUTYL | 8/92 | 74 |
| 9 | isoxazole-CH₂- | 75/25 | 65 |
| 10 | 3-pyridyl-CH₂- | 8/92 | 37 |
| 11 | N-methylimidazole-CH₂- | 90/10 | 85 |
| 12 | 2,6-dimethylpyridyl-CH₂- (6-methyl-2-pyridyl-CH₂-) | 40/60 | 66 |
| 13 | CH₃—S-CH₂- | 1.5/98.5 | 76 |
| 14 | CH₃OC₂H₅O-CH₂- | 14/86 | 67 |
| 15 | pyridyl-CH₂- | 40/60 | 58 |

Table 2 is a compilation of the β/α yield, and the overall yield (in percent by weight) obtained in Examples 16 and 17, wherein R² is ethyl.

TABLE 2

FORMATION OF COMPOUND 12 WITH

R⁴—S(C=O)CHR² SILYL ENOL ETHERS

| EXAMPLE | R⁴ | B/A RATIO | YIELD(PBW) |
|---|---|---|---|
| 16 | t-BUTYL | 0/100 | 92 |
| 17 | 3-methyl-2-pyridyl-CH₂- | 100/0 | 78 |

The following examples illustrate the best mode for carrying out this invention.

EXAMPLE 1

A. Preparation of S-(2-picolyl)thiopropionate

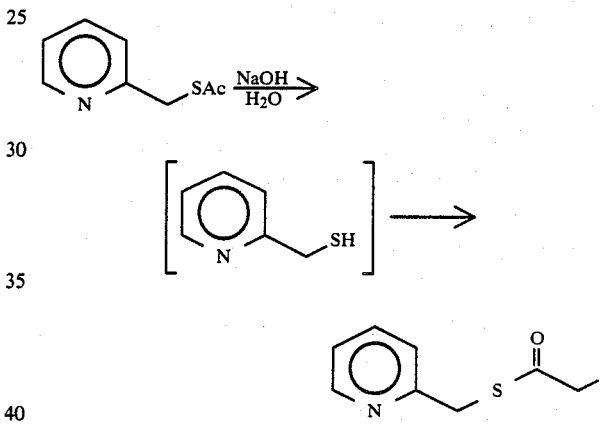

To a cold (ice bath) aqueous (600 mL) solution of NaOH (60.0 g, 1.5 mol) previously purged with a stream of N₂ (30 minutes) was added S-(2-picolyl)thioacetate (100 g, 0.600 mol). The heterogenous mixture was stirred for 1.5 hour during which it became homogeneous. It was then washed twice with 200 mL of methylene chloride neutralized (pH 7.5, ice bath) with cold concentrated HCl and extracted with methylene chloride (2×200 mL). The methylene chloride extracts were combined, washed with water (2×500 cc), brine (1×500 mL) and dried (Na₂SO₄). The volume of the organic solution was adjusted to 800 mL with CH₂Cl₂, cooled to 5° C. (ice bath), treated first with triethylamine (100.4 mL, 0.720 mol) and then propionyl chloride (57.4 mL, 0.660 mol) was added dropwise over a 20 minute period. The mixture was stirred for 30 minutes at 5° C., washed with cold water (2×400 mL), brine (1×400 mL), dried (Na₂SO₄), and the solvent was evaporated. The residue was diluted with ether, treated with neutral activated carbon and filtered through a Celite pad. The residue upon evaporation of the solvent was distilled under high vacuum to give title compound (94.7 g, b.p. 90°–98° C./0.6–0.3 mmHg).

B. Preparation of t-butyldimethylsilyl enol ether of S-(2-picolyl)thiopropionate

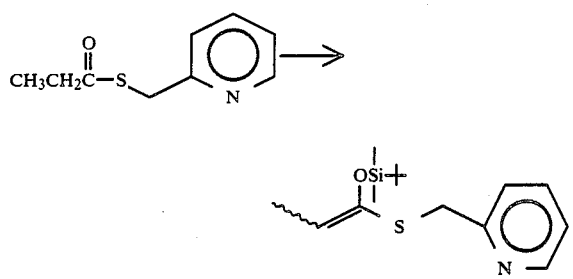

To a cold (−15° C.) methylene chloride (dried over 3A mole sieves, 500 mL) solution of S-(2-picolyl)thiopropionate (50.0 g, 0.276 mol) was added first triethylamine (69 mL, 0.495 mol) followed by the dropwise addition of TBDMS-triflate (95.3 mL, 0.415 mol). The mixture was stirred at room temperature for 3 hours after which TLC showed that no starting material was left. The solvent was evaporated at below 30° C. and the residue was taken up in petroleum ether. The cold mixture (solution—black gum) was washed with cold water (3×500 mL), cold brine (1×500 mL) dried (MgSO$_4$), treated with neutral activated carbon and filtered. Evaporation of the solvent gave title compound (68.19 g, 84% yield) as a red oil which was obtained as a mixture of 2 isomers (45:55); ir (CH$_2$Cl$_2$) $\nu_{max}$: 1635 (double bond) and 1595 cm$^{-1}$ (ar); $^1$Hmr (CDCl$_3$) δ: 8.55–6.95 (4H, m, ar), 4.98 (1H, 5 lines, isomeric H-vinyl), 4.04 and 3.97 (2H, 2s, isomeric —CH$_2$—), 1.54 and 1.55 (3H, 2d, J=6.9 Hz, J=6.7 Hz, isomeric —CH$_3$), 0.99 and 0.95 (9H, 2s, t-butyl), 0.19 and 0.23 ppm (6 H, 2s, dimethyl).

C. Preparation of (3S,4S)-3-[(1′R)-1′-t-butyldimethylsilyloxyethyl]-4-[(1″R)-1″-(2-picolylthiocarbonyl)-ethyl]-azetidin-2-one

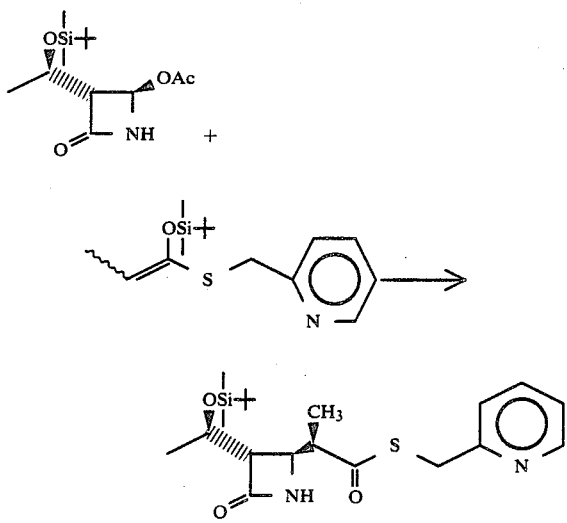

In a 1 L three neck flask, ZnCl$_2$ (23.8 g, 0.175 mol) was melted under N$_2$, allowed to cool at room temperature and pulverized. A solution of (3S,5R)-4-acetoxy-3-[(1′R-t-butyldimethylsilyloxyethyl)]-azetidin-2-one (50.0 g, 0.174 mol) in CH$_2$Cl$_2$ (375 mL) was added. The mixture was cooled at 5° C. (ice bath), treated with t-butyldimethylsilyl enol ether of S-(2-picolyl)thiopropionate (77.0 g, 0.261 mol) in CH$_2$Cl$_2$ (75 mL) and stirred at room temperature for 20 hours. It was treated again with the enol ether (12.75 g, 43 mmol) stirred for two more hours after which TLC revealed no more 4-acetoxyazetidinone. The mixture was washed with water (3×600 mL), brine, dried (Na$_2$SO$_4$) and the solvent was evaporated. The crude product obtained from a reaction on 81 g of 4-acetoxyazetidinone was purified on silica gel flash (2.8 L, petroleum). The title compound was eluted with ethyl acetate (88.6% oil, 80% crystalline, heptane) m.p.: 55°–58° C., and was shown to be a 87:13 mixture of β- and α-methyl isomers. β-methyl: ir (CH$_2$Cl$_2$) $\nu_{max}$: 3410 (N-H), 1765 (β-lactam), 1682 (thioester) and 1594 cm (ar); $^1$Hmr (CDCl$_3$) δ: 8.57–7.24, (4H, m, ar), 5.82 (1H, s, N-H), 4.30 (2H, s, —CH$_2$), 4.30–4.00 (1H, m, H-1,), 3.88 (1H, dd, J=2.2 Hz, J=6.4 Hz, H-4), 3.15–2.7 (2H, m, H-3, —CH—C—S—), 1.25 (3H, d, J=6.9 Hz, CH$_3$-2′), 1.07 (3H, d, J=6.3 Hz, —CH$_3$), 0.86 (9H, s, t-butyl) and 0.05 ppm (6H, dimethyl-Si-). α-methyl: ir (CH$_2$Cl$_2$) $\nu_{max}$: 3410 (N-H), 1765 (β-lactam C=O) and 1780 cm$^{-1}$ (thioester); $^1$Hmr (80 MHz, CDCl$_3$) δ: 8.55, 8.54, 8.50, 8.49 (1H, m, H-arom) 7.75, 7.72, 7.65, 7.62, 7.55, 7.53 (1H, m, H-arom), 7.22–7.00 (2H, m, H-arom), 6.21 (1H, 6s, N-H), 4.42, 4.29, 4.25 (2H, part of Abq, J=14 Hz, CH$_2$—S), 4.17, 4.09, 4.08 (1H, m, part of H′), 3.78, 3.75, 3.66, 3.63 (1H, dd, J=2.0 Hz, J=9.6 Hz, H-4), 2.95–2.55 (2H, m, H-3, H-1″), 1.31, 1.22 (3H, d, J=7.0 Hz, CH$_3$), 1.26, 1.18 (3H, d, J=6.2 Hz, CH$_3$), 0.87 (9H, s, t-butyl-Si) and 0.07 ppm [6H, (CH$_3$)$_2$-Si].

EXAMPLE 2

A. Preparation of S-(2-furylmethyl)thiopropionate

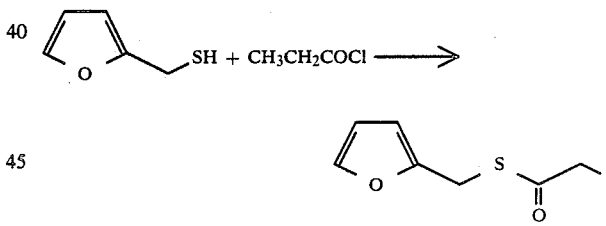

A cold (ice bath) solution of furfuryl mercaptan (75.6 mL, 750 mmol) in CH$_2$Cl$_2$ (750 mL) was treated with propionyl chloride (65.1 mL, 750 mmol) followed by the dropwise addition of triethylamine (14.2 mL, 875 mmol). The mixture was stirred at room temperature (22° C.) for 1.5 hour, diluted with CH$_2$Cl$_2$ (250 mL) and successively washed with water, 1N aqueous HCl, water, 1M aqueous NaHCO$_3$, water and brine. The organic solution was dried (MgSO$_4$), evaporated, diluted with ether (500 mL), and treated with neutral activated charcoal. The residue (88 g, 69%) upon evaporation of solvent was distilled to give the title compound 19.5 g, b.p. 64°–67°/0.3 mm Hg). When this reaction was repeated on a 43.8 g scale and stirred for 70 hours, it gave title material in a much better yield (48.6 g, 75%). ir (CH$_2$Cl$_2$) $\nu_{max}$: 1690 cm$^{-1}$ (C=O thioester); $^1$Hmr (60 MHz, CDCl$_3$) δ: 7.32 (1H, m, H-4), 6.27 (2H, m, H-3,4), 4.17 (2H, s, CH$_2$), 2.55 (2H, q, J=7 Hz, CH$_2$) and 1.17 ppm (3H, t, J=7 Hz, CH$_3$).

B. Preparation of t-butyldimethylsilyl enol ether of S-(2-furylmethyl)thiopropionate

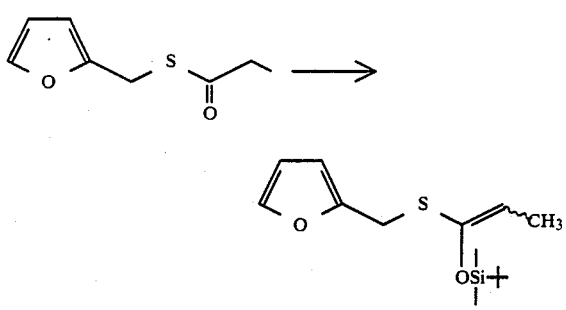

A cold (MeOH-ice bath) solution of S-(2-furylmethyl)thiopropionate (42.5 g, 250 mmol) in $CH_2Cl_2$ (400 mL) was treated first with triethylamine (87.5 mL, 625 mmol), then dropwise with TBDMS-triflate (115 mL, 500 mmol). The mixture was stirred at 22° C. for 2 hours, diluted with a 1:1 mixture of cold ether-petroleum ether (1.2 L), washed with cold water (2×500 mL), cold brine, dried ($MgSO_4$) and treated with activated neutral charcoal to give the title material (68.4 g, 96%), which was a mixture of geometric isomers as shown by $^1$Hmr; ir (neat) $\nu_{max}$: 1690 cm$^{-1}$ (thioester C=O); $^1$Hmr (60 MHz, $CDCl_3$) δ: 7.3 (1H, bs, H-5), 6.2 (1H, m, H-4), 6.1 (1H, m, H-3), 5.0 and 4.95 (1H, 2q, J=7 Hz, H-4), 3.87, 3.80 (2H, 2s, $CH_2$), 1.52 and 1.50 (3H, d, J=7 Hz, $CH_3$), 0.9 (9H, s, t-butyl-Si) and 0.15 ppm (6H, s, $(CH_3)_2$-Si).

C. Preparation of (3S,4S)-3-[(1'R)-1'-t-butyldimethylsilyloxyethyl]-4-[(1''R and S)-1''-(2-furanylmethylthiocarbonyl)-ethyl]-azetidine-2-one

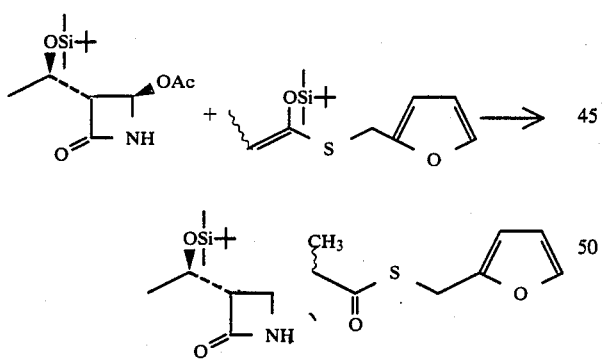

To freshly melted zinc chloride (6.8 g, 50 mmol) in $CH_2Cl_2$ (150 mL) was added at 5° C. (ice bath) (3S,4R)-4-acetoxy-3-[(1'R)-1'-t-butyldimethylsilyloxyethyl]azetidin-2-one (14.37 g, 50 mmol) and the t-butyldimethylsilyl enol ether of S(2-furyl-methyl)thiopropionate (28.4 g, 100 mmol) in $CH_2Cl_2$ (50 mL). The mixture was stirred at 22° C. for 18 hours, diluted with a 1:1 mixture of ether-ethyl acetate (500 mL), washed with water (2×500 mL) and brine (1×500 mL) and dried ($MgSO_4$). The solvent was evaporated and the residue was passed on a flash silica gel (250 g) pad (petroleum ether/ether: 7/3 and 1:1) to the give title material (19.49 g, 100%) as a 85:15 mixture of α- and β-methyl isomers;

ir ($CH_2Cl_2$) $\nu_{max}$: 3410 (NH), 1765 (β-lactam C=O) and 1685 cm$^{-1}$ (thioester C=O); $^1$Hmr (80 MHz, $CDCl_3$) δ: 7.33 (1H, m, H-arom), 6.32–6.18 (2H, m, H-arom), 5.90 (0.85H, b.s. NH), 5.75 (0.15H, shoulder, N-H), 4.32, 4.24, 4.10, 3.0 (1H, m, part of H-1'), 4.16 (2H, s, $CH_2$), 3.87 (0.15H, dd, H-4 β-methyl), 3.74 (0.85H, dd, J=2.1 Hz, J=9.5 Hz, H-4 α-methyl), 3.0–2.5 (zH, m, H-3 and H-1''), 1.26 (3H, d, J=7.0 Hz, $CH_3$), 1.22 (3H, d, J=6.3 Hz, $CH_3$), 0.87 (9H, s, t-butyl-Si) and 0.07 ppm (6H, s, $(CH_3)_2OSi$);. Anal. calcd for $C_{19}H_{31}NO_4SSi$: C 57.40, H 7.86, N 3.52; found: C 57.80, H 7.94, N 3.49.

EXAMPLE 3

A. Preparation of dimethylaminoethylthiopropionate

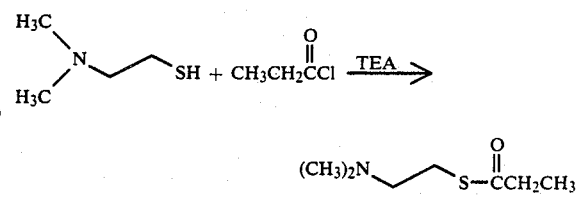

A cold (ice bath) solution of dimethylaminoethyl mercaptan (3.54 g, 25.0 mmol) in $CH_2Cl_2$ (50 mL) was treated dropwise with triethylamine (3.5 mL, 25 mmol) and stirred for 15 minutes. The cold solution was treated dropwise with propionyl chloride (2.3 mL, 26.5 mmol) followed by the dropwise addition of triethylamine (3.9 mL, 28 mmol). The reaction mixture was then allowed to warm up to room temperature and stirred for 1.5 hour. The mixture was washed with cold water (2×25 mL), brine and dried over $MgSO_4$. The residue obtained upon solvent evaporation was distilled to give the title compound (b.p. 46°–50° C./0.5 mm Hg, Yield: 1.7 g, (42%); ir ($CH_2Cl_2$) $\nu_{max}$: 1690 cm$^{-1}$ (thioester C=O); $^1$Hmr (60 MHz, $C_3D_6O$) δ: 2.95 (2H, q, J=7 Hz, $CH_3\underline{CH_2}$), 2.52 (4H, t, J=7 Hz, $CH_2$), 2.22 (6H, s, N-$CH_3$) and 1.1 ppm (3H, t, J=7 Hz, $\underline{CH_3}CH_2$).

B. Preparation of t-butyldimethylsilyl enol ether of dimethylaminoethylthiopropionate

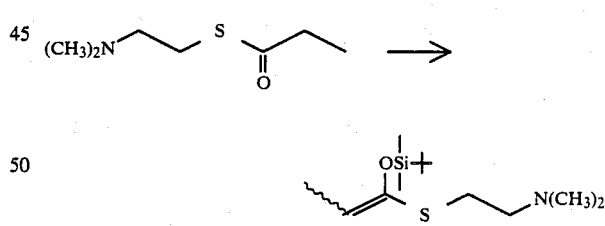

A cold (MeOH-ice) solution of dimethylaminoethylthiopropionate (805 mg, 5 mmol) in $CH_2Cl_2$ (10 mL) was treated dropwise first with triethylamine (1.4 mL, 10 mmol) and TBDMS-triflate (1.9 mL 8.3 mmol). The reaction mixture was stirred for 1.5 hour at 22° C., diluted with a 1:1 mixture of ether-petroleum ether, washed with cold water (2×25 mL), brine (1×25 mL), dried ($MgSO_4$). The solvent was evacuated in vacuo to give title compound as a 1:1 geometric mixture (1.4 g, 100%); ir ($CH_2Cl_2$) $\nu_{max}$: 3040–2780 (CH) and 1682 cm$^{-1}$ (olefin); $^1$Hmr (60 MHz, $C_3D_6O$) δ: 5.07 and 5.0 (1H, 2q, J=7.0 Hz, -H), 3.0–2.32 (4H, m, $CH_2$), 2.20 (6H, s, N-$(CH_3)_2$), 1.85, 1.75 (3H, 2d, J=7.0 Hz, $CH_3$), 0.95, 0.92 (9H, 2s, t-Bu-Si), and 0.022, 0.018 ppm (6H, 2s, $(CH_3)_2$-Si).

C. Preparation of (3S,4S)-3-[(1'R)-1'-t-butyldimethylsilyloxyethyl)-4-(1"R and S)-1"-(dimethylaminoethylthiocarbonyl)ethyl]-azetidine-2-one

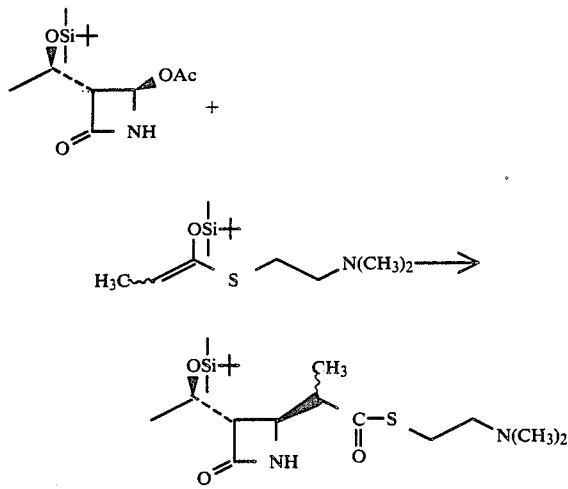

Zinc chloride (272.5 mg, 2 mmol) was freshly fused (under N$_2$) with a flame and allowed to cool down at room temperature. CH$_2$Cl$_2$ (8 mL) was added and the mixture was cooled to 5° C. (ice). Then (3S,4R)-3-[(1'-R-1'-t-butyldimethylsilyloxyethyl)]-4-acetoxyazetidin-2-one (575 mg, 2 mmol) was added followed by a solution of t-butyldimethylsilyl enol ether of dimethylaminoethylthiopropionate (1.1 g, 4.0 mmol) in CH$_2$Cl$_2$ (2 mL). The mixture was stirred at about 22° C. for 18 hours, diluted with a 1:1 mixture of ether-ethylacetate (30 mL), washed with water (1×25 mL), 1M aqueous NaHCO$_3$ (2×25 mL) brine (1×25 mL) and dried (MgSO$_4$). The residue obtained upon solvent evaporation was poured on a flash silica gel column (20 g) and was eluted with a 50% i-propanol-ethyl acetate mixture to give the title material as a 1:1 mixture of α- and β-methyl as estimated by $^1$Hmr; (0:1, 382 mg,; 49%) $\nu_{max}$: 3410 (N-H), 1765 (β-lactam C=O) and 1680 cm$^{-1}$ (thioester C=O); $^1$Hmr (80 MHz, C$_3$D$_6$O) δ: 7.25 (1H, b.s., N-H), 4.32–4.05 (1H, m, H-1'), 3.79 (0.5H, dd, J=2.1 Hz, J=5.3 Hz, H-4 of 1"-β-methyl), 3.68 (0.5H, dd, J=2.1 Hz, J=7.0 Hz, H-4 of 1"-α-methyl), 3.10–2.75 (4H, m, CH$_2$-N, H-3 and H-1"), 2.51, 2.43, 2.42, 2.34, 2.33, (2H, m, CH$_2$-S), 2.19 (6H, s, N-(CH$_3$)$_2$), 1.27, 1.11, 1.10 (6H, superimposed d, J=6.8 Hz, J=7.3 Hz, CH$_3$), 0.89 and 0.88 (9H, 2s, t-bu-Si), 0.11 and 0.08 ppm (6H, 2s, (CH$_3$)$_2$-Si).

EXAMPLE 4

A. Preparation of t-butyldimethylsilyl enol ether of 3-methyl-2-(propionylthio-methyl)-pyridine

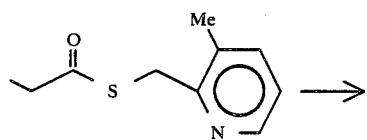

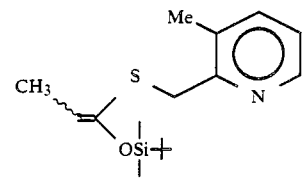

A cold (acetone dry-ice bath) solution of 3-methyl-2-(propionylthio-methyl)-pyridine (3.30 g, 16.9 mmol) in dry THF (50 mL) was treated dropwise with a 1M THF solution of lithium hexamethyl disilazane (18.6 mL, 18.6 mmol), and stirred for 5 minutes. The resulting enolate was treated with TBDMS-triflate (436 mL, 18.6 mmol), stirred for 30 minutes and quenched with 1M aqueous NaHCO$_3$ (50 mL). The mixture was diluted with ether (400 mL) and the phases were separated. The organic layer was washed with cold water (2×200 mL), brine (200 mL) and dried (MgSO$_4$). The solvent was evaporated to give the title material (5.2 g, 100%) as a 7.5/2.5 ratio of geometric isomers. Part of this mixture (1.6 g) was passed through a flash silica gel (160 g) chromatography column (25% ether, petroleum ether) to give pure isomer A (Rf. 0.75, 25% ether petroleum ether, 230 mg) and pure isomer B (Rf 0.68, 25% ether-petroleum ether, 570 mg); Isomer A, ir (CH$_2$Cl$_2$) $\nu_{max}$: 1635 cm$^{-1}$ (olefin); $^1$Hmr (CDCl$_3$, 80 MHz), δ: 8.40–8.34 (1H, m, H-aromatic), 7.37–7.06 (2H, m, H-aromatic), 5.03 (1H, d, J=7.0 Hz, olefinic-H), 4.10 (2H, s, CH$_2$), 2.38 (3H, s, CH$_3$), 1.56 (3H, d, J=6.8 Hz, CH$_3$, 0.96 (9H, s, t-butyl-Si) and 0.20 ppm (6H, s, (CH$_3$)$_2$-Si); isomer B, ir (CH$_2$Cl$_2$) $\nu_{max}$: 1635 cm$^{-1}$ (olefin); $^1$Hmr (80 MHz, CDCl$_3$) δ: 8.39, 8.34 (1H, m, H-aromatic), 7.37–6.95 (2H, m, H-aromatic), 5.00 (1H, q, J=6.8, olefinic-H), 4.04 (2H, s, CH$_2$), 2.35 (3H, s, CH$_3$), 1.34 (3H, d, J=6.8 Hz, CH$_3$), 0.97 (9H, s, t-butyl-Si) and 0.21 ppm (6H, s, (CH$_3$)$_2$-Si).

B. Preparation of (3S,4S)-3-[(1'R)-1'-t-butyldimethylsilyloxyethyl]-4-[(1"R)-1"-(3-methylpyridine-2-methylthiocarbonyl)-ethyl]-azetidin-2-one

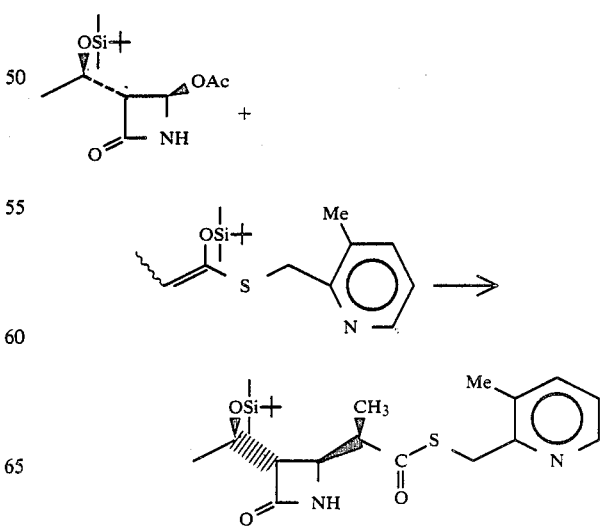

To freshly fused $ZnCl_2$ (2.90, 21.3 mmol) under $N_2$ was added (3S,4R)-4-acetoxy-3-[(1'R)-1'-t-butyldimethylsilyloxyethyl]-azetidin-2-one (3.06 g, 10.7 mmol) in $CH_2Cl_2$ (100 mL). The mixture was cooled to 0° C. and treated dropwise with the t-butyldimethylsilyl enol ether of 3-methyl-2-(propionylthio-methyl)-pyridine (6.60 g, 21.3 mmol) in $CH_2Cl_2$ (100 mL) and stirred for 20 hours at 22° C. The mixture was diluted with ethyl acetate (250 mL), washed with cold water (2×300 mL), brine (1×300 mL), dried ($MgSO_4$) and flushed down under vacuum. The residue was triturated with petroleum ether (20 mL) to give pure solid title material (3.19 g). The mother liquor was concentrated (3.5 g) to give a residue which was passed through a flash silica gel (140 g) column (20% $CH_3CN/CH_2Cl_2$-EtOAc) to give more crystalline title material (1.18 g, combined yield: 4.37 g, 97%). Inspection of the $^1$Hmr spectrum shown the presence of only the β-methyl isomer; ir ($CH_2Cl_2$) $\nu_{max}$: 3410 (N-H), 1765 (β-lactam C=O) and 1680 $cm^{-1}$ (thioester C=O); $^1$Hmr (80 Hz, $CDCl_3$) δ: 8.48–8.40 (1H, m, H-aromatic), 7.60–7.52 (1H, m, H-aromatic), 7.27–7.07 (1H, m, H-aromatic), 5.95 (1H, b.s., N-H), 4.38 (2H, s, $CH_2$), 4.15 (1H, center of dq, J=6.3 Hz, J=4.5 Hz, H-1'), 3.88 (1H, dd, J=2.2 Hz, J=5.5 Hz, H-4), 3.1–2.5 (2H, m, H-1" and H-3), 2.39 (3H, s, $CH_3$), 1.26 (3H, d, J=6.9 Hz, $CH_3$), 1.10 (3H, d, J=6.3 Hz, $CH_3$), 0.85 (9H, s, t-butyl-Si) and 0.05 (6H, s, $(CH_3)_2$-Si); Anal. calcd for $C_{21}H_{34}N_2O_3SSi$: C 59.68, H 8.11, N 6.63; found: C 59.87, H 7.97, N 6.66.

When isomer A of the silyl enol ether of 3-methyl-2-(propionylthiomethyl)-pyridine was reacted with 4-acetoxy-azetidin-2-one, the β-methyl was obtained as the major isomer, contaminated with only 16% of the corresponding α-isomer (see Example 5A). With isomer B, only the β-methyl isomer was obtained (see Example 5B).

Part C of Example 4 (which follows) illustrates the saponification shown in Step (C) of Diagram 1.

C. Preparation of (3S,4S)-3-[(1'R)-1'-t-butyldimethylsilyloxyethyl]-4-[(1"R)-1"-carboxyethyl]-azetidin-2-one

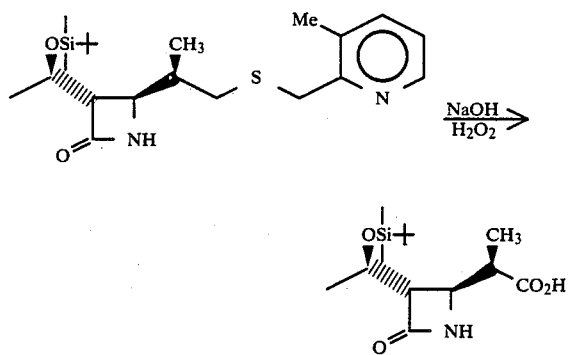

A cold (ice bath) THF (4 mL) solution of (3S,4S)-3-[(1'R)-1'-t-butyldimethylsilyloxyethyl]-4-[(1"R)-1"-(3-methylpyridin-2-methylthiocarbonyl)-ethyl]-azetidine-2-one (211 mg, 0.5 mmol) was treated first with $H_2O_2$ (30% v/v, 0.0086 mL, 1 mmol) and dropwise with 1.0N aqueous NaOH (1 mL, 1 mmol). The mixture was stirred for 10 minutes (ice bath), diluted with ethyl acetate (40 mL) and acidified with 1N aqueous HCl (20 mL). The organic phase was washed with water, aqueous $NaHSO_3$ (1M, 20 mL), water (20 mL), brine (20 mL) and dried ($MgSO_4$). Evaporation of ethyl acetate gave the β-methyl carboxylic acid (136 mg, 90%) with i.r. and $^1$Hmr data identical to that reported by Merck's scientists in *Heterocycles*, Volume 21, no. 1, page 29 (1984).

EXAMPLE 5A

Experimental conditions with Isomer A from Example 4

To freshly fused $ZnCl_2$ (41 mg, 0.33 mmol) under $N_2$ was added at 0° C. (3S,4R)-4-acetoxy-3-[(1'R)-1'-t-butyldimethylsilyloxyethyl]-azetidine-2-one (86 mg, 0.33 mmol) in $CH_2Cl_2$ (1 mL) and dropwise isomer A of the silyl enol ether (102 mg, 0.33 mL) in $CH_2Cl_2$ (2 mL). The mixture was stirred for 20 hours at about 22° C., and then diluted with ethyl acetate (25 mL), washed with water (2×15 mL), brine (15 mL), dried ($MgSO_4$) and flashed down under vacuum to give an oil (120 mg). The oil was passed through a flash silica gel (4 g) chromatography column (20% $CH_3CN/CH_2Cl_2$-EtOAc). A 9/1 mixture of β/α isomers, (42 mg, 33%) was obtained, as observed by $^1$Hmr; characteristic of the α-isomers in the $^1$Hmr spectrum: (80 MHz, $CDCl_3$). δ: 6.42 (b.s., N-H), 3.67 (dd, J=2 Hz, J=9 Hz, H-4), 1.23 (d, J=6.0 Hz, $CH_3$).

EXAMPLE 5B

Experimental Conditions with Isomer B from Example 4

The experimental conditions were identical to those used for isomer A. However only the β-methyl isomer product was obtained (70 mg, 55%, 100% β-isomer).

EXAMPLE 6

A. Preparation of t-butyldimethylsilyl enol ether of 2-thiophene-methylthiopropionate

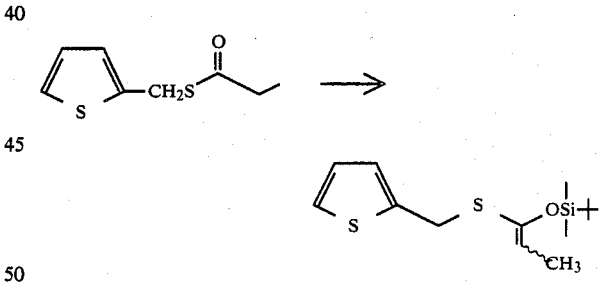

A cold (ice-MeOH bath) solution of 2-thiophenemethyl thiopropionate (373 mg, 2 mmol) in $CH_2Cl_2$ (3 mL) was treated with triethylamine (0.7 mL, 5 mmol) and dropwise with TBDMS-triflate (0.92 mL, 4 mmol). The mixture was stirred for 3 hours at 22° C., diluted with cold ether (5 mL), washed with cold water (2×20 mL), cold brine (1×20 mL) and dried ($Na_2SO_4$). The mixture was then evaporated under vacuum to give the title material (595 mg, 99%) as a yellow oil in a 7:3 mixture of geometric isomers, as shown by $^1$Hmr. $^1$Hmr (80 MHz, $CDCl_3$) δ: 7.20, 7.05 (1H, m, H-aromatic), 6.92–6.72 (2H, m, H-aromatic), 5.04 (0.7H, q, J=6.9 Hz, olefinic-H), 4.95 (0.3H, q, J=7 Hz, olefinic H), 4.11 (1.4H, s, $CH_2$), 4.05 (0.6H, s, $CH_2$), 1.60 (2.1H, d, J=6.8 Hz, $CH_3$), 1.56 (0.9H, d, J=7, $CH_3$), 0.96, (9H, s, t-butyl-Si) and 0.19 ppm (6H, s, $(CH_3)_2$-Si).

B. Preparation of (3S,4S)-3-[(1′R)-1′-t-butyldimethylsilyloxyethyl]-4-[(1″R and S)-1″-(2-thiophene)-methylthiocarbonylethyl)]-azetidine-2-one

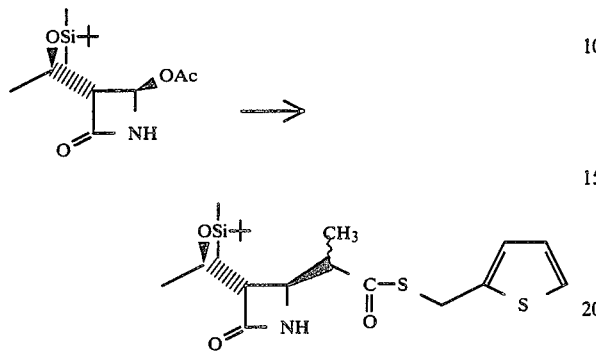

To freshly fused ZnCl₂ (173 mg, 2 mmol) in CH₂Cl₂ (8 mL) was added at 0° C. (ice bath) (3S,4R)-4-acetoxy-3-[(1′R)-1′-t-butyldimethylsilyloxyethyl]-azetidin-2-one (575 mg, 2 mmol) and the t-butyldimethylsilyl enol ether of 2-thiophenmethyl thiopropionate (1.11 g, 3.7 mmol) in CH₂Cl₂ (2 mL). The mixture was stirred at 22° C. for 18 hours, diluted with ethyl acetate (40 mL), washed with water (2×40 mL), brine (1×40 mL) and dried (Na₂SO₄). The solvent was evaporated to leave a yellow oil (1.3 g) which was passed through a flash silica gel (40 g) column (50% ether-petroleum ether) to give the crystalline title material, (700 mg, 84%). HPLC determined the title material to be a 81:19 mixture of α- and β-methyl isomers; ir (CH₂Cl₂) $\nu_{max}$: 3410 (NH), 1765 (β-lactam C=O) and 1680 cm⁻¹ (ester C=O); ¹Hmr (80 MHz, CDCl₃) δ: 7.25–7.1 (1H, m, aromatic-H), 6.95–6.8 (2H, m, aromatic-H), 5.85 (0.8H, b.s. NH), 5.8 (0.2H, shoulder, NH), 4.32 (2H, s, CH₂), 4.15 (1H, center of 5 lines, H-1′), 3.87 (0.2H, dd, J=2 Hz, J=6 Hz, H-4 β-methyl), 3.72 (0.8H, dd, J=2 Hz, J=9 Hz, H-4 α-methyl), 3–2.5 (2H, m, H-3 and H-1″), 1.27 (3H, d, J=7 Hz, CH₃), 1.22 (3H, d, J=7 Hz, CH₃), 1.10 (0.6H, d, J=7 Hz, CH₃), 0.87 (9H, s, t-butyl-Si) and 0.08 ppm (6H, s, (CH₃)₂-Si); Anal. calcd for C₁₉H₃₁NO₃S₂Si: C 55.17, H 7.55, N 3.39; found: C 55.48, H 7.65, N 3.47.

EXAMPLE 7

A. Preparation of t-butyldimethylsilyl enol ether of phenyl thiopropionate

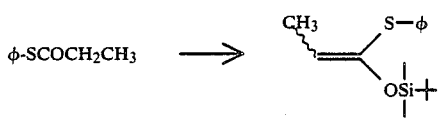

A cold (ice-MeOH bath) solution of phenyl thiopropionate (332 mg, 2 mmol) was treated first with triethylamine (0.70 mL, 5 mmol) and dropwise with TBDMS-triflate (0.92 mL, 4 mmol). The mixture was allowed to warm up to 22° C. and then stirred for 3 hours. The mixture was diluted with ether (15 mL), washed with cold water (2×20 mL), brine (1×20 mL), dried (Na₂SO₄) and treated with neutral activated charcoal to give title material (550 mg, 98%) as a yellow oil.

B. Preparation of (3S,4S)-3-[(1′R)-1′-t-butyldimethylsilyloxyethyl]-4-[(1″R and S)-1″-(phenylthiocarbonyl)-ethyl]-azetidin-2-one

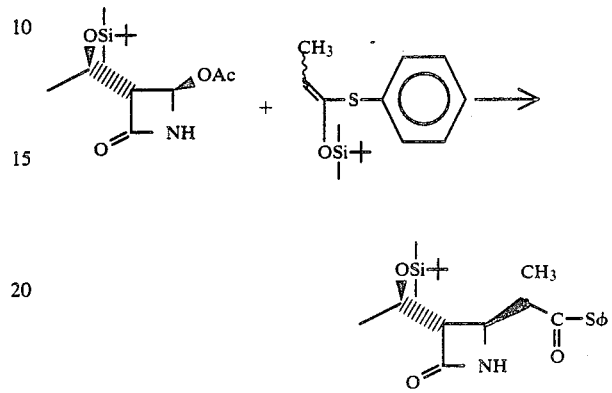

To cold (ice bath) freshly fused ZnCl₂ (136 mg, 1 mmol) in CH₂Cl₂ (3 mL) was added (3S,4R)-4-acetoxy-3-[(1′R)-1′-t-butyldimethylsilyloxyethyl]-azetidin-2-one (287 mg, 1 mmol) and the t-butyldimethylsilyl enol ether of phenyl thiopropionate (550 mg, 2 mmol). The mixture was stirred for 18 hours at 22° C., diluted with ethyl acetate (15 mL), washed with cold water (2×20 mL), brine (1×20 mL), dried (Na₂SO₄) and passed through a flash silica gel (20 g) column (50% ether/petroleum ether) to give the title material (349 mg, 91%) as a 9:1 mixture of α/β isomers as shown by HPLC; ir (CH₂Cl₂) $\nu_{max}$: 3410 (NH), 1765 (β-lactam C=O) and 1680 cm⁻¹ (ester C=O); ¹Hmr (80 MHz, CDCl₃) δ: 7.41 (5H, s, H-arom), 5.96, 5.7 (1H, 2 b.s., NH), 4.18 (1H, center of 5 lines, J=5.8, H-1′), 3.80 (center of dd, H-4 β-methyl), 3.77 (1H, dd, J=2.0 Hz, J=9.5 Hz, H-4 α-methyl), 3.0–2.55 (2H, m, H-1″ and H-3), 1.33 (3H, d, J=7.2 Hz, CH₃), 0.87 (9H, s, t-butyl-Si), and 0.07 ppm (6H, s, (CH₃)₂-Si); Anal. calcd for C₂₀H₃₁NO₃SSi: C 61.03, H 7.94, N 3.56; found: C 61.40, H 8.04, N 3.57.

EXAMPLE 8

A. Preparation of t-butyldimethylsilyl enol ether of t-butyl thiopropionate

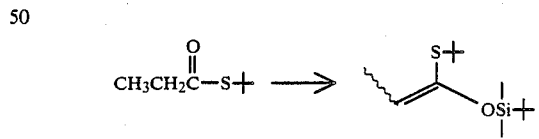

A cold (ice-MeOH) solution of t-butyl thiopropionate (2.93 g, 20 mmol) in CH₂Cl₂ (40 mL) was treated with triethylamine (5.0 mL, 36 mmol) and dropwise with TBDMS-triflate (6.9 mL, 30 mmol). The mixture was stirred at 22° C. for 4 hours., then evaporated, diluted with petroleum ether (50 mL), washed with cold water (2×60 mL) brine (1×60 mL), dried (MgSO₄) and treated with neutral activated charcoal. Evaporation of the solvent gave a colorless oil (5.1 g, 98%) as a 8:2 mixture of geometric isomers, as estimated by ¹Hmr; ir (CH₂Cl₂) $\nu_{max}$: 1625 cm⁻¹ (olefin); ¹Hmr (80 MHz, CDCl₃) δ: 5.75 (0.8H, q, J=6.8 Hz, olefinic-H) 5.23

(0.2H, q, J=7.0 Hz, olifinic H), 1.73 (2.4H, d, J=6.9 Hz, CH₃), 1.62 (0.6H, d, J=6.9, CH₃), 1.36 (7.2H, s, t-butyl-Si), 1.32 (1.8H, s, t-butyl-Si), 0.95 and 0.93 (9H, 2s, t-butyl-Si) and 0.18 and 0.15 ppm (6H, 2s, (CH₃)₂Si).

B. Preparation of (3S,4S)-3-[(1′-R)-1′-t-butyldimethylsilyloxyethyl]-4-[(1″R and S)-1″-(t-butylthiocarbonyl)-ethyl]-azetidin-2-one

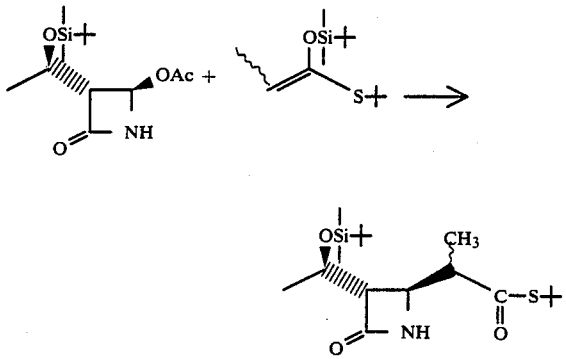

To freshly melted ZnCl₂ (636 mg, 4.70 mmol) under N₂ atmosphere was added (3S,4R)-4-acetoxy-3[(1′R)-1′-t-butyldimethylsilyloxyethyl]azetidin-2-one (1.34 g, 4.7 mmol) in CH₂Cl₂ (10 mL). The mixture was cooled to 5° C. (ice bath), treated with the t-butyldimethylsilyl enol ether of t-butyl thiopropionate (1.82 g, 7 mmol) in CH₂Cl₂ (5 mL) and stirred for 17 hours at 22° C. Since TLC of the reaction mixture indicated the presence of 4-acetoxyazetidinone, more enol ether (547 mg, 2.1 mmol) in CH₂Cl₂ (2 mL) was added. The reaction mixture was stirred for 4 hours, washed with cold water (2×30 mL), brine (1×30 mL), dried (Na₂SO₄). The residue was passed on a flash silica gel (80 g) column (2 and 5% CH₃CN/CH₂Cl₂) to give the title compounds. HPLC indicated a 92/8 mixture of α- and β-methyl; ir (CH₂Cl₂) ν$_{max}$: 3410 (NH), 1765 (β-lactam C=O) and 1675 cm⁻¹ (thioester C=O); ¹Hmr (80 MHz, CDCl₃) δ: 5.90 (1H, bs, NH-α-methyl) 5.80 (1H, shoulder, NH-β-methyl), 4.17 (1H center of 5 lines, J=5.7 Hz, H-1′), 3.85 (1H, dd, J=2 Hz, J=6 Hz, H-4 β-methyl), 3.70 (1H, dd, J=2.0 Hz, J=9.4 Hz, H-4 of α-methyl), 3–2.35 (2H, m, H-1″ and H-3), 1.55 (1 line of d, part of CH₃), 1.46 (²⁹H, s, Si-t-butyl and 1 line of CH₃), 1.23 (3H, d, J=6.5 Hz, CH₃), 0.88 (9H, s, t-butyl-Si), and 0.07 ppm (6H, s, (CH₃)₂Si); Anal. calcd for C₁₈H₃₅NO₃SSi: C 57.86, H 9.44, N 3.75; found: C, 58.12, H 9.37, N 3.73.

EXAMPLE 9

A. Preparation of t-butyldimethylsilyl enol ether of isothiazolyl-3-methyl thiopropionate

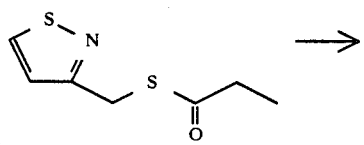

-continued

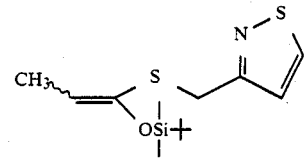

A cold (ice-MeOH bath) solution of isothiazolyl-3-methyl thiopropionate* (375 mg, 2 mmol) in CH₂Cl₂ (5 mL) was treated with triethylamine (0.71 mL, 5 mmol) and dropwise with TBDMS-triflate (0.94 mL, 4 mmol). The mixture was stirred at 22° C. for 1 hour, diluted with cold ether (25 mL), washed with cold water (2×15 mL), brine (1×10 mL); dried (MgSO₄) and treated with activated neutral carbon to give the title compound (532 mg, 92%) as a yellow oil. ¹Hmr revealed a 1:1 mixture of geometric isomers; ir (neat) ν$_{max}$: 1635 cm⁻¹ (olefin); ¹Hmr (80 MHz, CDCl₃) δ: 8.58–8.53 (1H, m, H-aromatic), 7.25–7.17 (1H, m, H aromatic), 5.03 (0.5H, q, J=7 Hz, olefinic-H), 4.95 (0.5H, q, J=7. Hz, olefinic H), 4.10 and 4.03 (2H, 2s, CH₂), 1.59 (1.5H, d, J=6.9 Hz, CH₃), 1.55 (1.5H, d, J=6.7 Hz, CH₃), 0.95 (9H, s, t-butyl-Si, and 0.09 ppm (6H, s, (CH₃)₂-Si).

*Prepared from the displacement of the corresponding mesylate with thiopropionic acid.

B. Preparation of (3S,4S)-3-[(1′R)-1′-t-butyldimethylsilyloxyethyl]-4-[(1″R and S)-1″-(isothiazol-3-methylthiocarbonyl)-ethyl]azetidin-2-one

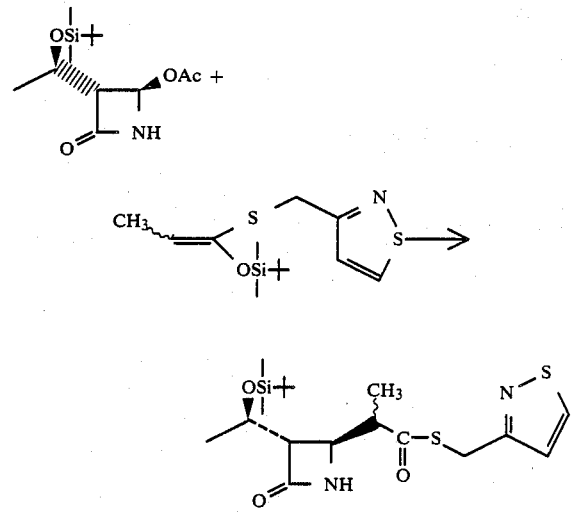

To freshly fused ZnCl₂ (136 mg, 1 mmol) under N₂ was added (3S,4R)-4-acetoxy-3-[(1′R)-1-t-butyldimethylsilyloxyethyl]-azetidin-2-one (287 mg, 1 mmol) in CH₂Cl₂ (3 mL). The mixture was cooled at 5° C. (ice bath) and the t-butyldimethylsilyl enol ether of 3-isothiazolyl-methyl thiopropionate (540 mg, 1.8 mmol) in CH₂Cl₂ (3 mL) was added in. It was stirred for 19 hours at 22° C. and more ZnCl₂ (136 mg, 1 mmol) was added in. The mixture was stirred for an additional 5 hours, diluted with ethyl acetate (25 mL), washed with water (2×10 mL), brine (10 mL), dried (MgSO₄). The residue after evaporation of the solvent was passed through a flash silica gel (25 g) column (5%-25% CH₃CN/CH₂Cl₂) to give the title material as an oil (270 mg, 65%) which slowly crystallized upon standing. ¹Hmr analysis of the spectrum showed a 25.75 mixture of α- (25) and β-isomer (75); ir (CH₂Cl₂) $\theta_{max}$: 3410 (N-H), 1770 (β-lactam C=O) and 1685 cm⁻¹ (thioester C=O), ¹Hmr (80 MHz, CDCl₃) δ: 8.63, 8.57 (1H 2 lines, J=4.7 Hz, H-aromatic), 7.18, 7.13 (1H, 2 lines, J=4.7 Hz, H-aromatic), 6.0 (0.25H, b.s. N-H), 5.79 (0.75H, b.s., NH), 4.31 (2H, s, CH₂), 4.24, 4.18, 4.16, 4.10 (1H, 4 lines, part of H-1'), 3.89 (0.75H, dd, J=2.1 Hz, J=Hz, H-4 β-methyl), 3.72 (0.25H, dd, J=2 Hz, J=10, H-4 α-methyl), 3.03-2.75 (2H, m, H-3 and H-1''), 1.26 (3H, d, J=6.9 Hz, CH₃), 1.22 (0.75H, d, J=6.1 Hz, CH₃), 1.10 (2.25 J=6.3 Hz, CH₃), 0.86 (9H, s, t-butyl-Si), and 0.06 ppm (6H, s, (CH₃)₂-Si); Anal. calc'd for C₁₈H₃₀N₂O₃S₂Si: C 52.14, H 7.29, N 6.76; found: C 52.51, H 7.36, N 6.56.

EXAMPLE 10

A. Preparation of t-butyldimethylsilyl enol ether of S-(3-picolyl)thiopropionate

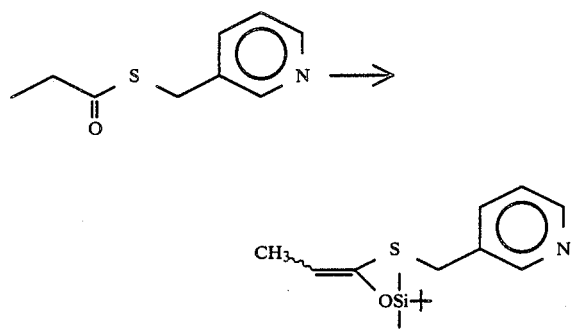

A cold (ice-MeOH bath) solution of S-(3-picolyl)thiopropionate (1.45 mg, 8 mmol) in CH₂Cl₂ (20 mL) was treated with triethylamine (2.8 mL, 20 mmol) and dropwise with TBDMS-triflate (3.7 mL, 16 mmol). The mixture was stirred at 22° C. for 3 hours. Then more triethylamine (0.56 mL, 4 mmol) and TBDMS triflate (0.92 mL, 4 mmol) were added and the mixture was stirred for 1 hour. This process was repeated again. The mixture was diluted with cold ether (80 mL), washed with water (2×100 mL), brine (1×100 mL), dried (MgSO₄), treated with neutral activated charcoal. The solvent was evaporated to leave a pale yellow oil (2.34 g, 99%). The ¹Hmr showed a 45:65 ratio of geometric isomers; ¹Hmr (80 MHz, CDCl₃) ν: 8.45-8.3 (2H, m, aromatic-H), 7.60-7.35 (1H, m, aromatic-H), 7.2 7.0 (1H, m, aromatic H), 4.97 (0.45H, q, J=7.0 olefinic H), 4.84 (0.55H, q, J=7 Hz, olefinic-H), 3.78 (0.9H, s, CH₂), 3.70 (1.1H, s, CH₂), 1.52, 1.49, 1.84, 1.80 (6H, 6 lines of CH₃, 2CH₃), 0.95-0.92 (9H, 2s, t-butyl-Si) and 0.15-0.07 ppm (6H, 2s, (CH₃)₂-Si).

B. Preparation of (3S,4S)-3-[(1'R)-1'-t-butyldimethylsilyloxyethyl]-4-[(1''R and S)-1''-(3-picolylthiocarbonyl)-ethyl]-azetidin-2-one

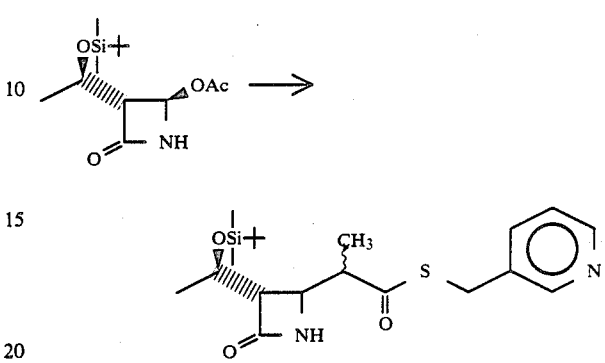

To freshly fused ZnCl₂ (273 mg, 2 mmol) in CH₂Cl₂ (10 mL) was added at 5° C. (ice bath) (3S,4R)-4-acetoxy[(1'R)-1'-t-butyldimethylsilyloxyethyl]-azetidin-2-one (575 mg, 2 mmol) and the t-butyldimethylsilyl enol ether of S-(3-picolyl)thiopropionate (1.1 g, 3.7 mol). The mixture was stirred at 22° C. for 18 hours, diluted with EtOAc, washed with water (2×50 mL), brine (1×50 mL) and dried (MgSO₄). Evaporation of the solvent gave a residue which was passed through a flash silica gel (50 g) column (EtOAc) to yield the title material (300 mg, 37%) as an oil. HPLC and ¹Hmr analysis revealed a 92/8 ratio of α- and β-methyl isomers: ir (neat) $\nu_{max}$: 3480 and 3210 (broad shoulder, NH), 1760 (β-lactam C=O) and 1682 cm⁻¹ (ester C=O); ¹Hmr (80 MHz, CDCl₃) δ: 8.55-8.45 (2H, m, H-aromatic), 7.64-7.52 (1H, m, H-aromatic), 7.29-7.14 (1H, m, H-aromatic), 5.95 (1H, b.s. NH), 4.23, 4.16 (part of H-1'), 4.10 (2H, s, CH₂), 3.94 (0.1H, dd, J=2.3 Hz, J=7.6 Hz, H-4-β-methyl), 2.74 (0.9H, dd, J=2.1, J=9.4, H-4-α-methyl), 3.2-2.5 (2H, m, H-3 and H-1''), 1.26 (3H, d, J=7.1 Hz, CH₃), 1.21 (3H, d, J=6.2 Hz, CH₃), 1.06 (0.3H, d, J=6.3 Hz), CH₃ β-methyl), 0.086 (9H, s, t-butyl-Si) and 0.06 ppm (6H, s, (CH₃)₂-Si); Anal. calcd for C₂₈H₃₂N₂O₃SSi: C 58.78, H 7.89, N 6.86; found: C 58.38, H 8.02, N 6.93.

EXAMPLE 11

A. Preparation of t-butyldimethylsilyl enol ether of 1-methyl-2-(propionylthio-methyl)-imidazole

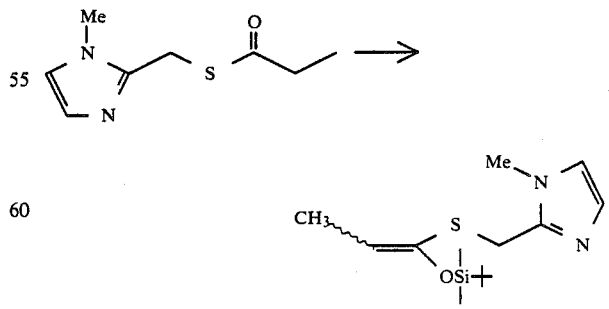

A cold (ice-MeOH bath) solution of 1-methyl-2-(propionylthio-methyl)imidazole (370 mg, 2 mmol) in CH₂Cl₂ (5 mL) was treated with triethylamine (0.71 mL, 5 mmol) and dropwise with TBDMS-triflate (0.94 mL, 4 mmol). The mixture was stirred for 3 hours. Then more triethylamine (0.28 mL, 2 mmol) and TBDMS-triflate (0.47 mL, 2 mmol) were added and stirring was continued for 20 more hours. TLC indicated the presence of the starting material, thiopropionate. More triethylamine (0.28 mL, 2 mmol) and TBDMS-triflate (0.47 mL, 2 mmol) were added and followed by a 2 hour stirring period. This process was repeated twice. The mixture was diluted with cold ether (25 mL), washed with cold water (2×25 mL), brine (25 mL), dried (MgSO$_4$) and treated with activated carbon to give title material (580 mg, 100%) as a yellow oil.

Analysis of the $^1$Nmr spectrum indicated a 42/58 ratio of geometric isomer; ir (CH$_2$Cl$_2$) $\nu_{max}$: 1635 cm$^{-1}$ (olefin); $^1$Hmr (80 MHz, CDCl$_3$) δ: 6.95 (1H, s, H-aromatic), 6.80 (1H, s, H-aroma-tic), 5.05 and 5.03 (1H, 2q, J=7 Hz, olefinic-H), 3.67 (1.74H, s, N-Me), 3.64 (1.26H, s, N-Me), 1.58 (1.74H, d, J=6.9 Hz, CH$_3$), 1.55 (1.26H, d, J=6.8 Hz, CH$_3$), 0.95–0.90 (9H, 2s, t-Butyl-Si), 0.019–0.08 ppm (6H, 2s, (CH$_3$)$_2$-Si).

B. Preparation of (3S,4S)-3-[(1′R)-1′-t-butyldimethylsilyloxyethyl]-4-[(1″R)-1″-(1-meethylimidazol-2-yl)-meethylthiocarbonylethyl]azetidin-2-one

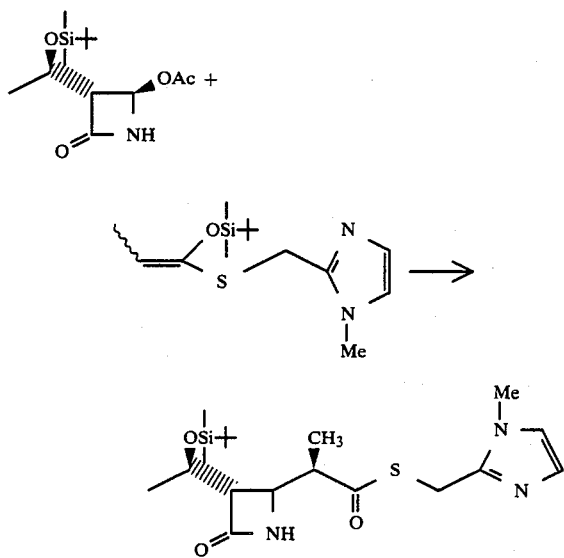

To a freshly fused ZnCl$_2$ (272 mg, 2 mmol) under N$_2$ was added (3S,4R)-4-acetoxy-3-[(1′R)-t-butyldimethylsilyloxyethyl]-azetidin-2-one (287 mg, 1 mmol) in CH$_2$Cl$_2$ (3 mL). The mixture was cooled (ice bath), treated with the t-butyldimethylsilyl enol ether of 1-methyl-2-(propionylthiomethyl)-imidazole (663 mg, 2 mmol) in CH$_2$Cl$_2$ (2 mL) and stirred for 20 hours at 22° C. The mixture was diluted with ethyl acetate (30 mL), washed with water (2×20 mL), brine (20 mL), dried (MgSO$_4$) and evaporated under vacuum to give a residue (850 mg). This residue was passed through a flash silica gel (35 g) column (1/1 acetone/ethyl acetate) to give the title material (350 mg, 85%) as a 90/10 mixture of β/α methyl*; ir (CH$_2$Cl$_2$) $\nu_{max}$: 3410 (N-H), 1770 (β-lactam C=O) and 1690 cm$^{-1}$ (thioester C=O); $^1$Hmr (80 MHz, CDCl$_3$)δ: 7.06 (1H, d, J−1.5 Hz, H-aromatic), 6.86 (1H, d, J=1.3 Hz, H-aromatic), 6.35 (0.1H, b.s., NH), 6.08 (0.9 H, bs, NH), 4.55 (2H, s, CH$_2$), 4.15 (1H, dq, J=7 Hz, J=5 Hz, H-1′), 3.83 (0.9H, dd, J=2.1 Hz, J=5.4 Hz, H-4 β-methyl), 3.67 (3H, s, N-CH$_3$), 3.15-2.5 (2H, m, H-3 - H-1″), 1.20 (3H, d, J=7.0 Hz, CH$_3$), 0.85 (9H, s, t-butyl-Si), and 0.05 ppm (6H, s, (CH$_3$)$_2$-Si); Anal. calcd for C$_{19}$H$_{33}$N$_3$O$_3$SSi: C 55.44, H 8.08, N 10.21; found: C 50.00, H 7.25, N 10.23.

*This was further proven by saponification of the thioester to the corresponding acid.

EXAMPLE 12

A. Preparation of t-butyldimethylsilyl enol ether of 6-methyl-2-(propionylthio-methyl)-pyridine

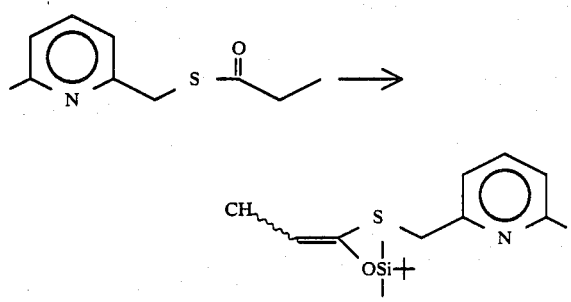

A cold (ice-MeOH bath) solution of 6-methyl-2-(propio-nylthio-methyl)-pyridine (370 mg, 1.9 mmol) in CH$_2$Cl$_2$ (5 mL) was treated with triethylamine (0.56 mL, 4 mmol) and dropwise with TBDMS-triflate (0.88 mL, 3.8 mmol). The mixture was stirred at 22° C. for 3 hours, diluted with cold ether (25 mL), washed with water (2×25 mL), brine (1×25 mL), dried (MgSO$_4$) and treated with neutral activated charcoal. Evaporation of the solvent gave title material (575 mg, 98%) as a yellow oil. $^1$Hmr spectrum releaved a 7/3 mixture of geometric isomer; ir (CH$_2$Cl$_2$) $\nu_{max}$: 1635 cm$^{-1}$ (olefin); $^1$Hmr (80 MHz CDCl$_3$) δ: 7.55-7.2 (1H, m, H-aromatic), 7.15–6.80 (2H, m, H-aromatic), 5.02 (0.3H, q, J=6.8 Hz, olefinic-H), 4.94 (0.7H, q, J=6.8 Hz, olefinic-H), 4.02 (0.6H, s, CH$_2$), 3.94 (1.4H, s, CH$_2$), 2.53 (3H, s, CH$_3$), 1.54 (3H, d, J=6.8 Hz, CH$_3$), 0.98, 0.94 (9H, 2s, t-butyl-Si), 0.18-0.09 (6H, 2s, (CH$_3$)$_2$-Si).

B. Preparation of (3S,4S)-3[(1′R)-1′-t-butyldimethylsilyloxyethyl]-4-[(1″R and S)-1″-(6-methylpyridin-2-yl)-methylthiocarbonylethyl-]azetidin-2-one

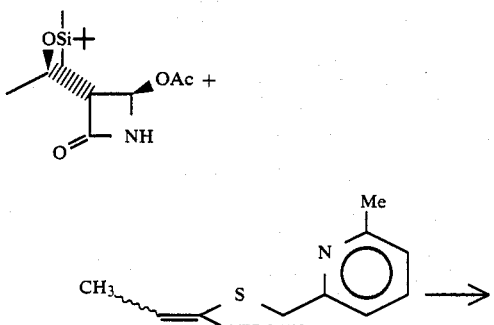

-continued

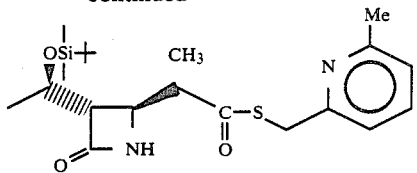

To cold (ice bath) freshly fused ZnCl₂ (136 mg, 1 mmol) in CH₂Cl₂ (3 mL) was added (3S,4R)-4-acetoxy-3-[(1′R)-1′-t-butyl-dimethylsilyloxyethyl]-azetidin-2-one (287 mg, 1 mmol) and the t-butyldimethylsilyl enol ether of 6-methyl-2-(propionylthio-methyl)-pyridine (560 mg, 1.8 mmol), in CH₂Cl₂ (3 mL). The mixture was stirred for 18 hours at 22° C., diluted with ethyl acetate (25 mL), washed with water (2×15 mL), brine (15 mL), dried (MgSO₄) and the solvent was evaporated. The residue (610 mg) was passed through a silica gel (25 g) column (EtOAc) to give title material (280 mg, 66%). ¹Hmr spectrum analysis revealed a 60/40 mixture of α/β methyl isomers: ir (CH₂Cl₂) $\nu_{max}$: 3410 (NH), 1765 (β-lactam C=O) and 1680 cm⁻¹ (thioester C=O); ¹Hmr (80 MHz, CDCl₃) δ: 7.65-7.50 (1H, m, H-aromatic), 7.25-7.03 (2H, m, H aromatic), 6.22 (0.6H, b.s. N-H α-methyl), 5.85 (0.4H, bs, N-H β-methyl), 4.33 (0.8H, s, CH₂), 4.30 (1.2H, s, CH₂), 4.24, 4.22, 4.16, 4.14, 4.09, 4.07, 4.01, 3.98 (part of dq, H-1′ α- and β-methyl), 3.86 (0.4H, dd, J=2.2 Hz, J=5.6 Hz, H-4 β-methyl), 3.70 (0.6H, dd, J=2.0 Hz, J=9.5 Hz, H-4 α-methyl), 3.06-2.5 (2H, m, H-3 and H-1″), 2.59 (3H, s, CH₃), 1.26 (1.8H, J=7.1 Hz, CH₃), 1.24 (1.2H, J=6.4 Hz, CH₃), 0.86 (9H, s, t-butyl-Si) and 0.06-0.04 (6H, 2s, (CH₃)₂-Si); Anal. calcd for C₂₁H₃₄N₂O₃SSi: C 59.68, H 8.11, N 6.63; found: C 59.84, H 8.24, N 6.66.

EXAMPLE 13

A. Preparation of methylthiomethyl thiopropionate

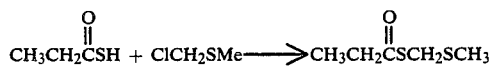

A cold (ice bath) solution of thiopropionic acid (360 mg, 4 mmol) in CH₂Cl₂ (5.0 mL) was treated with chloromethyl methylthioether (0.33 mL, 4 mmol) and triethylamine (0.7 mL, 5 mmol) and stirred for 30 minutes at 5° C. The cold bath was removed and the mixture was stirred for 30 minutes at about 22° C., diluted with CH₂Cl₂, washed successively with 1N aqueous HCl, water, 1M aqueous NaHCO₃, water and brine and dried (MgSO₄). The title compound was obtained as a yellow oil (510 mg, 85%); ir (CH₂Cl₂) $\nu_{max}$: 1695 cm⁻¹ (thioester C=O); ¹Hmr (60 MHz, CDCl₃) δ: 4.07 (2H, s, CH₂), 2.62 (2H, q, J=7 Hz, CH₂), 2.2 (3H, s, CH₃) and 1.2 ppm (3H, t, J=7 Hz, CH₃).

B. Preparation of t-butylsilyl enol ether of methylthiomethyl thiopropionate

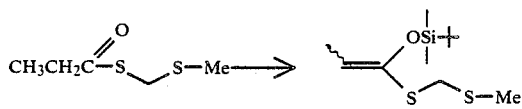

A cold (ice-MeOH) solution of methylthiomethyl thiopropionate (470 mg, 3.1 mmol) in CH₂Cl₂ (6 mL) was treated with triethylamine (0.84 mL, 6 mmol) and dropwise with TBDMS triflate (1.06 mL, 4.6 mmol). The mixture was stirred at 22° C. for 2.5 hours, diluted with ether (20 mL), washed with cold water (2×10 mL), brine (1×20 mL) and dried (MgSO₄). Evaporation of solvent gave title material (850 mg, 100%) as a yellow oil; ir (CH₂Cl₂) $\nu_{max}$: 1635 cm⁻¹ (olefin).

C. Preparation of (3S,4S)-3-[(1′R)-1′-t-butyldimethylsilyloxyethyl)]-4-[(1″S)-1″-(methylthiomethylthiocarbonyl)-ethyl]azetidin-2-one

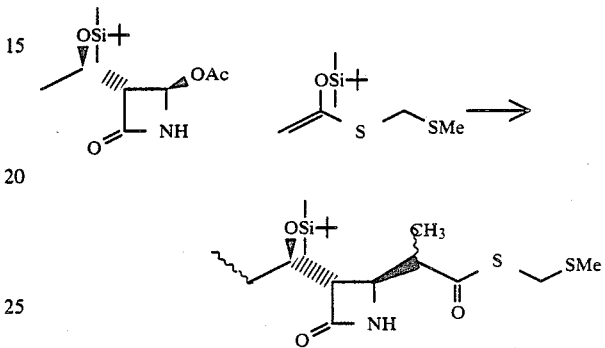

To a cold (5° C.) suspension of ZnCl₂ freshly melted (204.4 mg, 1.5 mmol) in methylene chloride (5 mL) was added (3S,4R)-4-acetoxy-3-[(1′R)-1′-t-butyldimethylsilyloxyethyl]azetidin-2-one (431 mg, 1.5 mmol). A solution of the t-butyldimethylsilyl enol ether of methylthiomethyl thiopropionate (595 mg, 2.25 mmol) in CH₂Cl₂ (1 mL) was then added. The mixture was stirred at 22° C. for 18 hours, diluted with ether (20 mL), washed with water (3×10 mL), brine and dried (MgSO₄). The residue obtained upon solvent evaporation was first purified on a flash silica gel pad (7 g, CH₂Cl₂—5% EtOAc/CH₂Cl₂) and then on preparative silica gel plate (5% EtOAc/CH₂Cl₂) to give the title material (429 mg, 76%) containing more than 98.5% of the α-methyl isomer as shown by the ¹Hmr spectrum; ir (CH₂Cl₂) $\nu_{max}$: 3410 (N-H), 1765 (β-lactam C=O) and 1680 cm⁻¹ (thioester C=O); ¹Hmr (80 MHz, CDCl₃) δ: 5.92 (1H, b.s., N-H), 4.18 (1H, center of 5 lines, J=5.5 Hz, J=6.1 Hz, H-1′), 4.02 (2H, s, CH₂), 3.75 (1H, dd, J=2.1 Hz, J=9.5 Hz, H-4), 3.1-2.5 (2H, m, H-3 and H-1″), 2.16 (3H, s, CH₃), 1.29 (3H, d, J=7.0 Hz, CH₃), 1.23 (3H, d, J=6.2 Hz, CH₃), 0.87 (9H, s, t-Bu-Si) and 0.07 ppm (6H, s, (CH₃)₂-Si).

EXAMPLE 14

A. Preparation of methoxyethoxymethyl thiopropionate

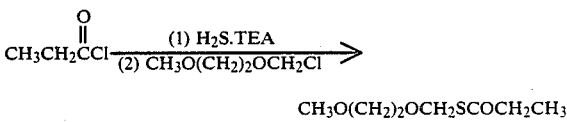

CH₃O(CH₂)₂OCH₂SCOCH₂CH₃

A cold (5° C.) solution of triethylamine (8.0 mL, 57 mmol) in CH₂Cl₂ (200 mL) was treated with a stream of H₂S for 30 minutes (keeping the temperature below 10° C.). To this solution was added dropwise propionyl chloride (3.7 mL, 40 mmol) in CH₂Cl₂ (50 mL). The mixture was stirred for 2.5 hours at 22° C., diluted with CH$_2$Cl$_2$ (100 mL), washed with 1N aqueous HCl (2×20 mL), water (2×20 mL), brine and dried (MgSO$_4$). Evaporation of the solvent gave thiopropionic acid (1.02 g, 28%). A solution of the thiopropionic acid (450 mg), in CH$_2$Cl$_2$ (5 mL) was cooled (5° C.) and treated with MEM-chloride (0.57 mL 5.0 mmol) and triethylamine (0.9 mL, 6.5 mmol). The mixture was stirred at 22° C. for 30 minutes, diluted with CH$_2$Cl$_2$, washed successively with 1N aqueous HCl, water, 1M aqueous NaHCO$_3$, brine and dried (MgSO$_4$) to give title material (850 mg, 95%) as an oil; ir (CH$_2$Cl$_2$) $\nu_{max}$: 1700 cm$^{-1}$ (thioester C=O); $^1$Hmr (60 MHz, CDCl$_3$) δ: 5.2 (2H, s, SCH$_2$O), 3.6 (4H, b.s. O(CH$_2$)$_2$O), 3.42 (3H, s, CH$_3$), 2.65 (2H, q, J=7 Hz, CH$_2$) and 1.2 ppm (3H, t, J=7 Hz, CH$_3$).

B. Preparation of t-butyldimethylsilyl enol ether of methoxyethoxymethyl thiopropionate

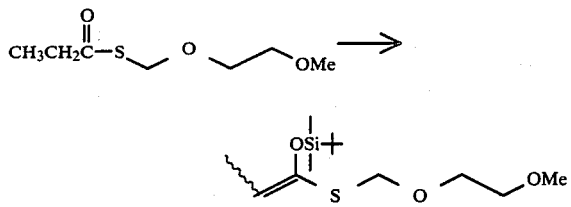

A cold (−15° C.) solution of methoxyethoxymethyl thiopropionate (623 mg, 3.5 mmol) in CH$_2$Cl$_2$ (7 mL) was treated with triethylamine (1 mL, 7.0 mmol) and TBDMS triflate (1.21 mL, 5.25 mmol). The mixture was stirred at 22° C. for 1.5 hour, diluted with a 1:1 mixture of ether-petroleum ether (20 mL), washed with water (2×20 mL) brine, dried MgSO$_4$) and treated with neutral activated charcoal. Evaporation of the solvent afforded the title material (1.1 g, 100%) as an oil; ir (CH$_2$Cl$_2$) $\nu_{max}$: 1635 cm$^{-1}$ (olefin).

C. Preparation of (3S,4S)-3-[(1′R)-1′-t-butyldimethylsilyloxyethyl)]-4-[(1″S and R)-1″-(methoxyethoxymethylthiocarbonyl)-ethyl]azetidin-2-one

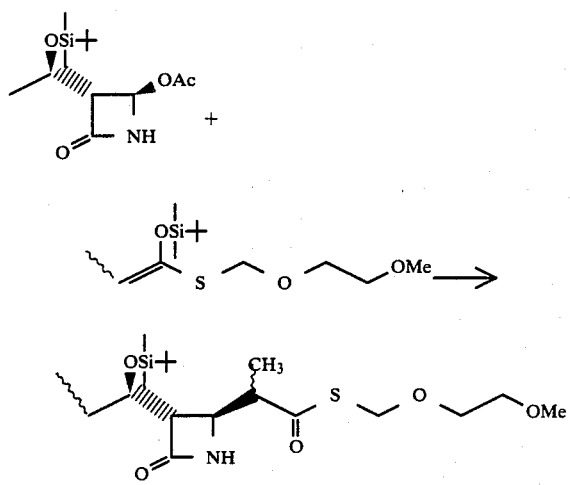

To freshly fused ZnCl$_2$ (204 mg, 1.5 mmol) in CH$_2$Cl$_2$ (5 mL), cooled to 5° C. was added (3S,4R)-4-acetoxy-3-[(1′R)-1′-t-butyldimethylsilyloxyethyl]-azetidin-2-one (431 mg, 1.5 mmol) and the t-butyldimethylsilyl enol ether of methoxyethoxymethyl thiopropionate (658 mg, 2.25 mmol) in CH$_2$Cl$_2$ (1 mL). The reaction mixture was stirred at 22° C. for 18 hours. Since TLC revealed the presence of 4-acetoxyazetidinone, more enol ether (146 mg, 0.5 mmol) was added to the mixture. It was then stirred for 1 hour, diluted with ether (20 mL), washed with water (2×20 mL), brine and dried (MgSO$_4$). The residue (990 mg) was passed on a flash silica gel (15 g) column (CH$_2$Cl$_2$-20% EtOAc/CH$_2$Cl$_2$) to give the title material (407 mg, 67%) as a colorless oil. HPLC analysis of the mixture showed a ratio of 86:14 of α- and β-isomers; ir (CH$_2$Cl$_2$) $\nu_{max}$: 3410 (N-H), 1765 (β-lactam C=O), 1690 cm$^{-1}$ (thio-ester C=O); $^1$Hmr (80 MHz, CDCl$_3$) δ: 6.10 and 5.75 (1H, 1 b.s., NH α and β), 5.25, 5.22, 5.17, 5.14, 5.11 and 4.92 (2H, ABq, S—CH$_2$—O), 4.27–3.95 (1H, 5 lines, H-1′), 3.85 (H-4-β-methyl), 3.67 (1H, dd, J=1.7 Hz, H-4-α-methyl), 3.60–3.38 (4H, m, O(CH$_2$)$_2$O), 3.36 (3H, s, OCH$_3$), 3.05–2.5 (2H, m, H-3 and H-1″), 1.28 (3H, d, J=7.1 Hz, CH$_3$), 1.23 (3H, d, J=6.1 Hz, CH$_3$), 0.87 (9H, s, t-butyl-Si) and 0.07 ppm (6H, s, (CH$_3$)$_2$Si).

EXAMPLE 15

A. Preparation of S-(4-picolyl)thiopropionate

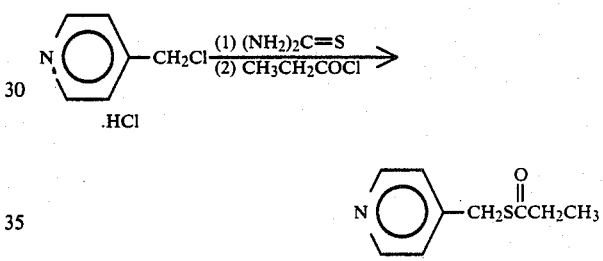

A solution of 4-picolyl chloride (5.0 g, 30.5 mmol) and thiourea (2.6 g, 33.5 mmol) in water (15 mL) was heated (90°–95° C.) for 2 hours. The solution was cooled to 5° C. (ice bath) and NaOH (3.7 g, 91.5 mmol) was added in small portions, while keeping the reaction mixture temperature below 20° C. The mixture (suspension) was stirred for 20 hours at about 22° C. (homogeneous), cooled at 5° C., diluted with THF and treated dropwise with propionyl chloride (2.64 mL, 30.5 mmol). The solution was stirred at 5° C. for 30 minutes, neutralized at pH 7 with 10% aqueous NaHCO$_3$ and extracted with ethyl acetate (4×25 mL). The organic extracts were combined, washed with water and brine, dried (MgSO$_4$) and treated with neutral activated charcoal. The residue obtained upon solvent evaporation was distilled (b.p. 110°-3° C./300 mm Hg) to give the title material (4.8 g, 87%); ir (CH$_2$Cl$_2$) $\nu_{max}$: 1695 cm$^{-1}$ (thioester C=O); $^1$Hmr (60 MHz, CDCl$_3$) δ: 8.55 (2H, b.d., arom.-H); 7.22 (2H, b.d., arom.-H), 4.10 (2H, s, CH$_2$-ar), 2.62 (2H, q, J=7.5 Hz, CH$_2$-CH$_3$) and 1.20 ppm (3H, t, J=7.5 Hz, CH$_3$).

B. Preparation of t-butyldimethylsilyl enol ether of S-(4-picolyl)thiopropionate

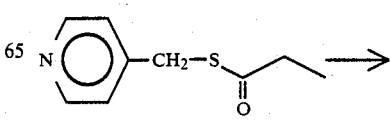

31
-continued

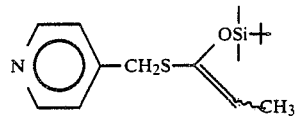

A cold (MeOH-ice) solution of S-(4-picolyl)thiopropionate (2.71 g, 15 mmol) in CH$_2$Cl$_2$ (30 mL) was treated dropwise with triethylamine (4.2 mL, 30 mmol) and TBDMS-triflate (5.8 mL, 25 mmol). The mixture was stirred at about 22° C. for 1.5 hour, diluted with a 1:1 mixture of ether:petroleum ether, washed with cold water (2×50 mL) brine (1×50 mL), dried (MgSO$_4$) and treated with neutral activated charcoal. The title compound was obtained upon solvent evaporation as an oil (5.0 g, 100%) and the $^1$Hmr clearly showed a major geometric isomer; ir (CH$_2$Cl$_2$) $\nu_{max}$: 1635 (olefin) and 1600 cm$^{-1}$ (aromatic); $^1$Hmr (60 MHz, CDCl$_3$) δ: 8.52 (2H, b.d., H arom.), 7.18 (2H, b.d., H arom.), 4.90 (1H, q, J=7 Hz, =H), 3.82 (0.1H, s, CH$_2$), 3.75 (0.9H, s, CH$_2$), 2.5 (3H, d, J=7 Hz, CH$_3$), 1.02 (9H, s, t-butyl-Si) and 0.25 (6H, s, (CH$_3$)$_2$Si). C. Preparation of (3S,4S)-3-[(1'-R)-1'-t-butyldimethylsilyloxyethyl)]-4-[(1''R and S)-1''-(4-picolylthiocarbonyl)-ethyl]-azetidin-2-one

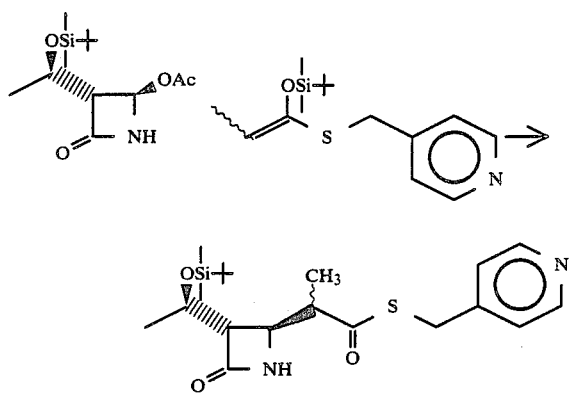

To freshly melted zinc chloride (272.5 mg, 2 mmol) under nitrogen atmosphere was added CH$_2$Cl$_2$ (8 mL). The mixture was cooled to 5° C., treated with (3S,4R)-4-acetoxy-3-[(1'R)-1'-t-butyldimethylsilyloxyethyl)]-azetidin-2-one (5.75 mg, 2 mmol) and the t-butyldimethylsilyl enol ether of S-(4-picolyl)thiopropionate (890 mg, 3 mmol) in CH$_2$Cl$_2$ (2 mL). The mixture was stirred for 18 hours at 22° C. Thin layer chromatography revealed the presence of 4-acetoxyazetidinone. More silyl enol ether (293 mg, 2 mmol) was added and the reaction mixture was stirred for 4 hours. It was diluted with a 1:1 mixture of ethyl acetate:ether, washed with cold water (2×25 mL), brine (1×25 mL) and dried (MgSO$_4$). The residue was purified on flash silica gel (25 g) column (ether—ethyl acetate) to give title material (471 mg, 58%) as a yellow oil. The $^1$Hmr spectrum showed a 6:4 mixture of α and β methyl; ir (CH$_2$Cl$_2$) $\mu_{max}$: 3410 (N-H), 1765 (β-lactam C=O) and 1685 cm$^{-1}$ (thioester C=O); $^1$Hmr (80 MHz), CDCl$_3$) δ: 8.61, 8.55, 8.53 (2H, b.d., arom. H), 7.33, 7.27, 7.25 (2H, b.d., arom. H), 5.98 (0.6H, b.s, N-H), 5.87 (0.4H, bs, N-H), 4.17–3.9 (1H, hidden m, H-1'), 4.09 (2H, s, CH$_2$), 3.86 (0.4H, dd, J=1 Hz, J=5.6 Hz, H-4 β-methyl), 3.73 (0.6 H, dd, J=2.1 Hz, J=9.3 Hz, H=4 α-methyl), 2.95–2.5 (2H, m, H-3 and H-1''), 1.27 (d, J=7.1 Hz, CH$_3$), 1.21 (d, J=6.1 Hz,

32
CH$_3$), 1.07 (d, J=6.3 Hz, CH$_3$), 0.87 (9H, s, t-butyl-Si) and 0.06 ppm (6H, s, (CH$_3$)$_2$-Si).

EXAMPLE 16

A. Preparation of t-butyldimethylsilyl enol ether of t-butyl thiobutyrate

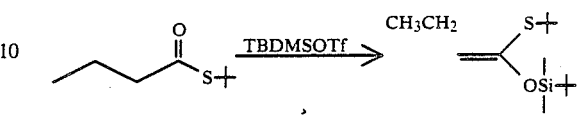

A cold (ice bath) solution of t-butylthiobutyrate (1.0 g, 6.2 mmol) was treated, as described with the corresponding thiopropionate (in part A of Example 8), with triethylamine (1.6 mL, 11.2 mmol) and TBDMS triflate (2.20 mL, 9.4 mmol) in CH$_2$Cl$_2$ (15 mL) to give the title material (1.7 g, 100%) as a 9/1 α/β mixture of geometric isomers; ir (neat) $\nu_{max}$: 1620 cm$^{-1}$ (olefin); 'Hmr (CDCl$_3$, 200 MHz) δ: 5.258 (0.9H, t, J=7.4 Hz, olefinic H), 5.149 (0.1H, t, J=7.2 Hz, olefinic H), 2.30–2.0 (2H, m, CH$_2$) 1.342 and 1.304 (9H, 2s, S-t-butyl), 0.95 and 0.162 (3H, part of t, CH$_3$), 0.912 and 0.842 (9H, 2s, Si-t-butyl) and 0.136 (6H, s, Si(CH$_3$)$_2$).

B. Preparation of (3S,4S)-3-[(1'R)-1'-t-butyldimethylsilyloxyethyl]-4-[(1''S)-1''-t-butylthiocarbonylpropyl]-azetidin-2-one

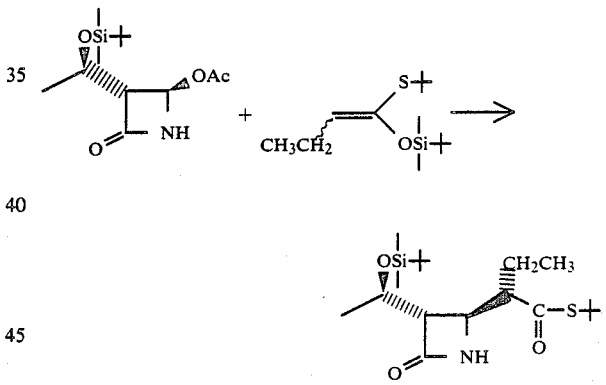

To freshly fused ZnCl$_2$ (845 mg, 6.2 mmol) under N$_2$ was added (3S,4R)-4-acetoxy-3-[(1'R)-1'-t-butyldimethylsilyloxyethyl]-azetidin-2-one (891 mg, 3.1 mmol) and the silyl enol ether of t-butyl thiobutyrate (1.7 g, 6.2 mmol) in CH$_2$Cl$_2$ (10 mL) at 5° C. The mixture was stirred and worked up under the same conditions as described for the corresponding α-methyl isomer in part B of Example 8 to give the title material (1.1 g, 92%) mp 102°–104° C. (EtOAc); ir (CH$_2$Cl$_2$) $\nu_{max}$: 3400 (NH), 1760 (C=O β-lactam) and 1670 cm$^{-1}$ (C=O thioester); $^1$Hmr (CDCl$_3$, 80 MHz) δ: 5.81 (1H, bs, NH), 4.128 (1H, 5 lines, J=5.9 Hz and 6.1 Hz, H-1'), 3.68 (1H, dd, J=2.0 Hz, J=9.4 Hz, H-4), 2.466 (1H, b and t, J=1.8 Hz, J=1.3 Hz and J=5.0 Hz, H-3), 2.477 and 2.454 (1H, dt, J=9.3 Hz, J=4.6 Hz, H-1''), 1.8–1.4 (2H, m, CH$_2$CH$_3$), 1.448 (9H, s, t-butyl-S), 1.205 (3H, d, J=6.3 Hz, CH$_3$), 0.936 (3H, t, J=7.4 Hz, CH$_3$), 0.851 (9H, s, t-butyl-Si) and 0.050, 0.046 (6H, 2s, CH$_3$Si).

Part C of this Example illustrates the saponification shown in Step (C) of Diagram 1.

C. Preparation of (3S,4S)-3-[(1'R)-1-t-butyldimethylsilyloxyethyl]-4-[1''S)-1''-carboxypropyl]-azetidin-2-one

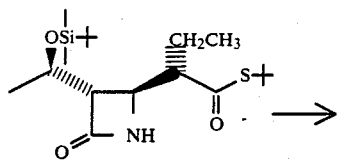

A cold (ice bath) THF solution of (3S,4S)-3-[(1'R)-1'-t-butyldimethylsilyloxyethyl]-4-[(1''S)-1''-t-butylthiocarbonylpropyl]-azetidin-2-one (194 mg, 0.500 mmol) was treated with $H_2O_2$ (30% v/v, 0.09 mL, 1.0 mmol) and 1N aqueous NaOH (1 mL, 1 mmol). The mixture was allowed to warm to room temperature (ca. 22° C.) and stirred for 48 hours. The reaction mixture was worked up to yield the title material (136 mg, 86%); m.p. 171°–74° C.; ir ($CH_2Cl_2$) $\nu_{max}$: 3480, 3380 (OH), 3400 (NH), 1760 (C=O β-lactam) and 1745 and 1710 cm$^{-1}$ (C=O acid); $^1$Hmr (CDCl$_3$ 200 MHz) δ: 6.25 (1H, bs, NH), 4.18 (1H, center of 5 lines, H-1'), 3.779 (1H, dd, J=1.9 Hz, J=9.4, H-4), 2.832 (1H, bd, J=4.34 Hz, H-3), 2.480 and 2.455 (2H, dt, J=4.9 Hz, J=9.2 Hz, H-1''), 1.676 (2H, m, CH$_2$), 1.244 (3H, d, J=7.2 Hz, CH$_3$), 1.014 (3H, t, J=7.4 Hz, CH$_3$), 0.875 (9H, s, t-butyl-Si) and 0.078 and 0.067 (6H, 2s, CH$_3$-Si).

EXAMPLE 17

A. Preparation of t-butyldimethylsilyl enol ether of 3-methyl-2-(butyrylthiomethyl)-pyridine

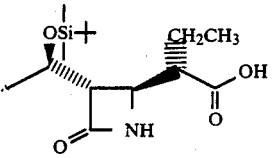

A cold (dry ice-acetone) THF (10 mL) solution of 3-methyl-2-(butyrylthiomethyl)-pyridine (1.032 g, 4.930 mmol) was treated, under the conditions described for the preparation of the corresponding propionylthio derivative (part A of Example 4), with lithium hexamethyldisilazane (5.42 mL, 5.42 mmol, 1.0M in THF) and TBDMS-triflate (1.24 mL, 5.42 mmol) to give the title material (1.84 g, 100%) as a 54/46 mixture of geometric isomers; ir (neat) $\nu_{max}$: 1620 cm$^{-1}$ olefin; $^1$Hmr (200 MHz, CDCl$_3$) δ: 8.370, 8.346, 7.412, 7.378, 7.066, 7.042, 7.029, 7.005 (3H, aromatic), 4.996 (0.46H, t, J=7.50 Hz, olefinic H), 4.890 (0.54H, t, J=7.18 Hz, olefinic H), 4.083 (0.96H, s, CH$_2$), 4.017 (1.06H, s, CH$_2$), 2.366 and 2.349 (3H, 2s, CH$_3$), 1.988 (2H, center of 5 lines, CH$_2$-CH$_3$), 0.9490 (9H, s, t-butyl), 0.8453 and 0.784 (3H, 2t, J=7.50 and 7.18 Hz, CH$_3$), and 0.134 ppm (6H, s, Si-CH$_3$).

B. Preparation of (3S,4S)-3-[(1'-R)-1'-t-butyldimethylsilyloxyethyl]-4-[(1''R)-1''-(3-methylpyridin-2-yl)-methylthiocarbonylpropyl]azetidin-2-one

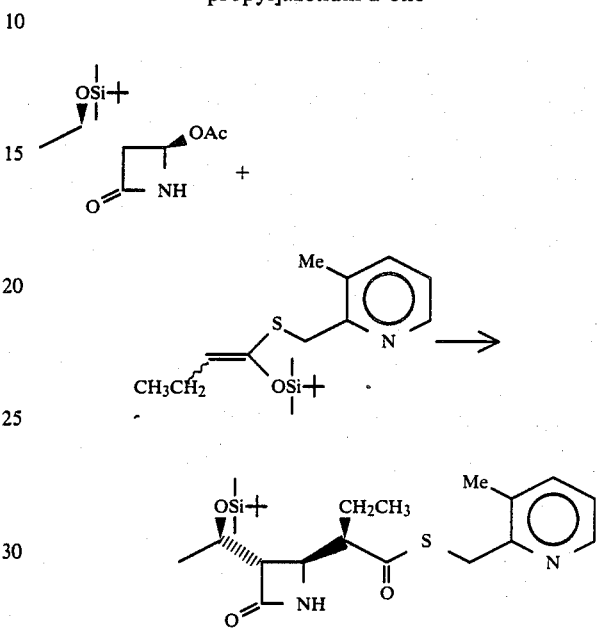

To freshly fused ZnCl$_2$ (674 mg, 4.93 mmol) under N$_2$ was added (3S,4R)-4-acetoxy-3-[(1'R)-1'-t-butyldimethylsilyloxyethyl]-azetidin-2-one (710 mg, 2.47 mmol) in CH$_2$Cl$_2$ (5 mL) and the t-butyldimethylsilyl enol ether of 3-methyl-2-(butyrylthiomethyl)-pyridine (1.6 g, 4.93 mmol) in CH$_2$Cl$_2$ (5 mL). The mixture was treated under the conditions described for the preparation of the corresponding β-methyl isomer (part B of Example 4). The title compound (β-ethyl) was obtained in excellent yield (78%, 837 mg) mp 70°–72° C. (EtOAc) no α-ethyl isomer was present; ir (CH$_2$Cl$_2$) $\nu_{max}$: 3400 (NH), 1755, 1680 cm$^{-1}$ (C=O); $^1$Hmr (CDCl$_3$, 200 MHz) δ: 8.36, 8.34, 7.45, 7.41, 7.12, 7.09, 7.08, 7.05 (3H, m, aromatic H), 5.856 (1H, bs, NH), 4.31 (2H, center of ABq, J=13.87 Hz, CH$_2$), 4.150 (1H, center of 9 lines, H-1'), 3.815 (1H, dd, J=2.05 Hz, J=7.08 Hz, H-4), 3.049 (1H, bt, J=2.5 Hz, H-3), 2.705 (1H, m, H-1''), 2.344 (3H, s, CH$_3$), 1.988–1.42 (2H, m, CH$_2$), 1.0379 (3H, d, J=6.36 Hz, CH$_3$), 0.957 (3H, t, J=7.42 Hz, CH$_3$), 0.837 (9H, s, t-butyl) and 0.0292 ppm (6H, s, CH$_3$Si).

C. Preparation of (3S,4S)-3-[(1'R)-1'-t-butyldimethylsilyloxyethyl]-4-[(1''R)-1''-carboxypropyl]-azetidin-2-one

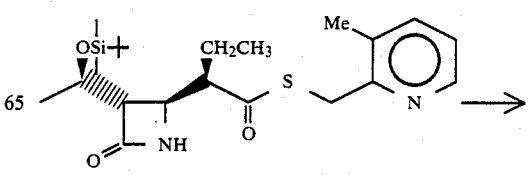

-continued

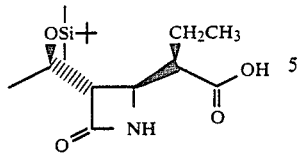

A cold (ice bath) THF (4 mL) solution of (B 3S,4S)-3-[(1'R)-1'-t-butyldimethylsilyloxyethyl]-4-[(1"R)-1"-(3-methylpyridin-2-yl)-methylthiocarbonylpropyl]-azetidin-2-one (437 mg, 1 mmol) was treated, as described previously for the corresponding β-methyl analog (part C of Example 4), with H$_2$O$_2$ (30%, 0.72 mL, 2 mmol) and 1N aqueous NaOH (2 mL, 2 mmol). The mixtrue was stirred at about 22° C. for 90 minutes and worked up to give pure title material (280 mg, 89%) m.p. 136°–138° C. (EtOAC); ir (Nujol) ν$_{max}$: 3400 (NH), 3480–2500 (OH), 1765 β-lactam C=O and 1745 and 1710 cm$^{-1}$ (C=O acid); 'Hmr (200 MHz, CDCl$_3$) δ: 6.28 (1H, 6S, NH), 4.21–4.15 (1H, m, H-1'), 3.86 (1H, dd, J=2.0 Hz, J=6.6 Hz, H-4), 3.10 (1H, 6t, J=2.6 Hz, H-3), 2.54 (1H, center of m, H-1"), 1.8–1.2 (2H, m, CH$_2$), 1.147 (3H, d, J=6.3 Hz, CH$_3$), 0.986 (3H, t, J=7.3 Hz, CH$_3$), 0.847 (9H, s, t-butyl) and 0.047, 0.040 (2s, 6H, CH$_3$Si).

What is claimed is:

1. A process for producing carbapenem intermediates of the formula

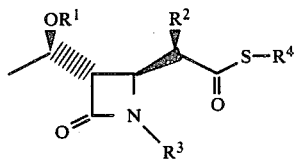

wherein
R$^1$ is hydrogen or a conventional hydroxy-protecting group,
R$^2$ is lower alkyl having from 1–6 carbon atoms,
R$^3$ is hydrogen, trimethylsilyl, triisopropylsilyl, triethylsilyl, t-butyldiphenylsilyl, t-butyldimethylsilyl, or (2,4,6-tri(t-butyl)phenoxy)dimethylsilyl,
R$^4$ is a group selected from pyrid-2-ylmethyl, 3-methylpyrid-2-ylmethyl, isothiazol-3-ylmethyl, and 1-methylimidazol-2-yl-methyl
which process comprises
(A) reacting a compound of the formula

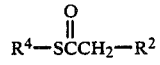

wherein R$^2$ and R$^4$ are as defined above, with a triorganosilyl triflate silylating agent in the presence of an organic base and an inert organic solvent to yield a silyl enol ether intermediate of the formula

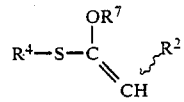

wherein R$^2$ and R$^4$ are as defined above, R$^7$ is the trioranosilyl residue of said triorganosilyl triflate silylating agent, and
(B) reacting Compound 8 with a compound of the formula

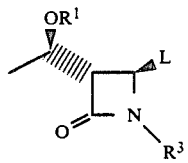

wherein R$^1$ is as defined above, and L is a leaving group capable of being displaced by nucleophilic substitution of Compound 8 in the presence of a Lewis acid catalyst.

2. The process of claim 1, wherein
L is acetoxy.
3. The process of claim 1, wherein
said organic base is a tertiary amine base.
4. The process of claim 1, wherein
said organic base is triethylamine.
5. The process of claim 1, wherein
said organic base is lithium hexamethyl disilasane.
6. The process of claim 1, wherein
said triorganosilyl triflate silylating agent is selected from the group consisting of trimethylsilyl trifluoromethanesulfonate, triisopropylsilyl trifluoromethanesulfonate, triethylsilyl trifluoromethanesulfonate, t-butyldimethylsilyl trifluoromethanesulfonate, t-butyldiphenylsilyl trifluoromethanesulfonate, and 2,4,6,-tri(t-butylphenoxy) dimethylsilyl trifluoromethanesulfonate.
7. The process of claim 6, wherein
said silylating agent is t-butyldimethylsilyl trifluoromethanesulfonate.
8. The process of claim 2, wherein
R$^2$ is methyl or ethyl, and
R$^3$ is hydrogen.
9. The process of claim 1, wherein
said Lewis acid catalyst is zinc chloride.
10. The process of claim 1, wherein
R$^2$ is methyl or ethyl.
11. The process of claim 1, wherein
R$^3$ is hydrogen.
12. The process of claim 8, wherein
R$^4$ is 3-methylpyrid-2-ylmethyl.
13. The process of claim 1, wherein
R$^4$ is 3-methylpyrid-2-ylmethyl.

* * * * *